United States Patent
Kim et al.

(10) Patent No.: US 11,521,391 B2
(45) Date of Patent: Dec. 6, 2022

(54) REFRIGERATOR, SERVER AND METHOD OF CONTROLLING THEREOF

(71) Applicant: SAMSUNG ELECTRONICS CO., LTD., Suwon-si (KR)

(72) Inventors: Tae-hoon Kim, Seoul (KR); Viktor Porokhonskyy, Kyiv (UA); Oleksandr Baiev, Seoul (KR); Mykhailo Klymenko, Kharkov region (UA); Yevhen Vahin, Kharkov (UA)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 21 days.

(21) Appl. No.: 16/433,107

(22) Filed: Jun. 6, 2019

(65) Prior Publication Data

US 2019/0384990 A1 Dec. 19, 2019

(30) Foreign Application Priority Data

Jun. 15, 2018 (KR) .................... 10-2018-0069078

(51) Int. Cl.
*G06K 9/62* (2022.01)
*H04N 5/247* (2006.01)
(Continued)

(52) U.S. Cl.
CPC ............ *G06V 20/52* (2022.01); *G06F 3/0482* (2013.01); *G06K 9/6201* (2013.01);
(Continued)

(58) Field of Classification Search
CPC .... G06K 9/00771; G06K 9/4604; G06K 9/54; G06K 9/6201; G06K 9/6257;
(Continued)

(56) References Cited

U.S. PATENT DOCUMENTS 9,195,960 B2 * 11/2015 Kim .................. F25D 29/00
9,965,798 B1 * 5/2018 Vaananen ............ F25D 27/005
(Continued)

FOREIGN PATENT DOCUMENTS

JP 2006-064320 A 3/2006
JP 2012-193873 A 10/2012
(Continued)

OTHER PUBLICATIONS

Cunningham et al., U.S. Appl. No. 62/613,886, filed Jan. 5, 2018. (Year: 2018).*
(Continued)

*Primary Examiner* — Behrooz M Senfi
*Assistant Examiner* — Kathleen M Walsh
(74) *Attorney, Agent, or Firm* — Sughrue Mion, PLLC

(57) ABSTRACT

A server includes a memory storing instructions and a processor configured to execute the instructions to obtain an inside-fridge image captured in a refrigerator by comparing a pre-stored image to the obtained inside-fridge image, identify whether a change area in which a change occurred in the obtained inside-fridge image is present in the obtained inside-fridge image, based on the change area being not present in the obtained inside-fridge image, obtain first food storage information, using a first result of recognizing the pre-stored image, based on the change area being present in the obtained inside-fridge image, obtain second food storage information, using the obtained first food storage information and a second result of recognizing an object included in the obtained inside-fridge image, and transmit, to the refrigerator, the obtained inside-fridge image and either one or both of the obtained first food storage information and the obtained second food storage information.

12 Claims, 15 Drawing Sheets

(51) Int. Cl.

| | | |
|---|---|---|
| *G06T 5/00* | (2006.01) | |
| *G06V 20/52* | (2022.01) | |
| *G16H 50/30* | (2018.01) | |
| *G06V 10/44* | (2022.01) | |
| *G06F 3/0482* | (2013.01) | |
| *G06V 20/68* | (2022.01) | |
| *H04L 67/02* | (2022.01) | |
| *G06Q 30/06* | (2012.01) | |
| *G09B 19/00* | (2006.01) | |
| *H04L 67/10* | (2022.01) | |
| *G06V 10/20* | (2022.01) | |

(52) U.S. Cl.
CPC ....... *G06K 9/6257* (2013.01); *G06Q 30/0641* (2013.01); *G06V 10/20* (2022.01); *G06V 10/44* (2022.01); *G09B 19/0092* (2013.01); *G16H 50/30* (2018.01); *H04L 67/02* (2013.01); *H04L 67/10* (2013.01); *H04N 5/247* (2013.01); *F25D 2400/36* (2013.01); *F25D 2700/06* (2013.01); *G06T 5/003* (2013.01); *G06T 2207/20192* (2013.01); *G06V 20/68* (2022.01)

(58) Field of Classification Search
CPC .. G06K 2209/17; G16H 50/30; G06F 3/0482; G06F 3/0486; G06F 3/04886; G06F 16/583; G06Q 30/0641; G06Q 30/0271; G06Q 50/10; G09B 19/0092; H04L 67/02; H04L 67/10; H04N 5/247; H04N 5/232; F25D 240/36; F25D 2700/06; F25D 2400/36; F25D 2400/361; F25D 2500/06; F25D 29/00; G06T 5/003; G06T 2207/20192; G06T 2207/20084; G06T 2207/20224; G06T 7/254; G06T 7/74; G06T 7/13
USPC .......................................................... 348/159
See application file for complete search history.

(56) References Cited

U.S. PATENT DOCUMENTS

| | | | | |
|---|---|---|---|---|
| 2007/0282506 A1* | 12/2007 | Breed | ................ | G06K 9/00838 701/45 |
| 2014/0297467 A1* | 10/2014 | Soller | ................... | H04L 65/403 705/26.8 |
| 2014/0313328 A1* | 10/2014 | Park | ........................ | F25D 29/00 348/143 |
| 2014/0313331 A1* | 10/2014 | Kim | ........................ | F25D 29/00 348/143 |
| 2015/0248754 A1* | 9/2015 | Graner | ............... | G06K 9/00771 382/103 |
| 2015/0278912 A1* | 10/2015 | Melcher | .................. | H04W 4/80 705/26.7 |
| 2015/0294450 A1* | 10/2015 | Eyring | ................... | A61B 5/486 382/110 |
| 2015/0363173 A1* | 12/2015 | Kurokawa | ................ | G06F 8/31 717/115 |
| 2016/0088262 A1* | 3/2016 | Lee | ........................ | F25D 29/00 704/275 |
| 2016/0132821 A1 | 5/2016 | Glasgow et al. | | |
| 2016/0182864 A1* | 6/2016 | Izawa | .................. | H04N 5/2256 348/159 |
| 2016/0217417 A1* | 7/2016 | Ma | ........................ | H04N 5/225 |
| 2016/0349072 A1* | 12/2016 | Yoshitomi | .......... | G01C 21/3602 |
| 2016/0358508 A1 | 12/2016 | Cheatham, III et al. | | |
| 2017/0219276 A1* | 8/2017 | Wang | ....................... | F25D 29/00 |
| 2017/0219279 A1 | 8/2017 | Chae et al. | | |
| 2018/0018443 A1* | 1/2018 | Cho | ....................... | G16H 20/30 |
| 2019/0034556 A1* | 1/2019 | Gu | ........................ | G06V 10/143 |
| 2019/0205821 A1* | 7/2019 | Werner | .................. | G01G 19/42 |
| 2019/0213443 A1* | 7/2019 | Cunningham | ....... | G06K 9/6256 |
| 2020/0363125 A1* | 11/2020 | Uchida | .................. | F25D 29/005 |
| 2021/0041159 A1* | 2/2021 | Uchida | .................. | G03B 29/00 |

FOREIGN PATENT DOCUMENTS

| | | | | |
|---|---|---|---|---|
| JP | 2014-196846 A | | 10/2014 | |
| JP | 2016-061556 A | | 4/2016 | |
| JP | 2017089913 A | * | 5/2017 | |
| KR | 10-2008-0030173 A | | 4/2008 | |
| KR | 20120117464 A | * | 10/2012 | ............ G06Q 50/10 |
| KR | 10-1756620 B1 | | 7/2017 | |
| KR | 10-2017-0115699 A | | 10/2017 | |
| KR | 10-2017-0137301 A | | 12/2017 | |
| WO | WO-2018016054 A1 | * | 1/2018 | ............ G06Q 50/10 |
| WO | WO-2018040105 A1 | * | 3/2018 | ............ F25D 11/00 |
| WO | WO-2018143550 A1 | * | 8/2018 | ............ F25D 23/04 |

OTHER PUBLICATIONS

Written Opinion (PCT/ISA/237) issued by the International Searching Authority in corresponding International Application No. PCT/KR2019/006850, dated Oct. 8, 2019.

International Search Report (PCT/ISA/210), issued by International Searching Authority in corresponding International Application No. PCT/KR2019/006850, dated Oct. 8, 2019.

Communication dated Apr. 29, 2021 issued by the European Intellectual Property Office in counterpart European Application No. 19819251.0.

\* cited by examiner

FIG. 8A
FIG. 8B
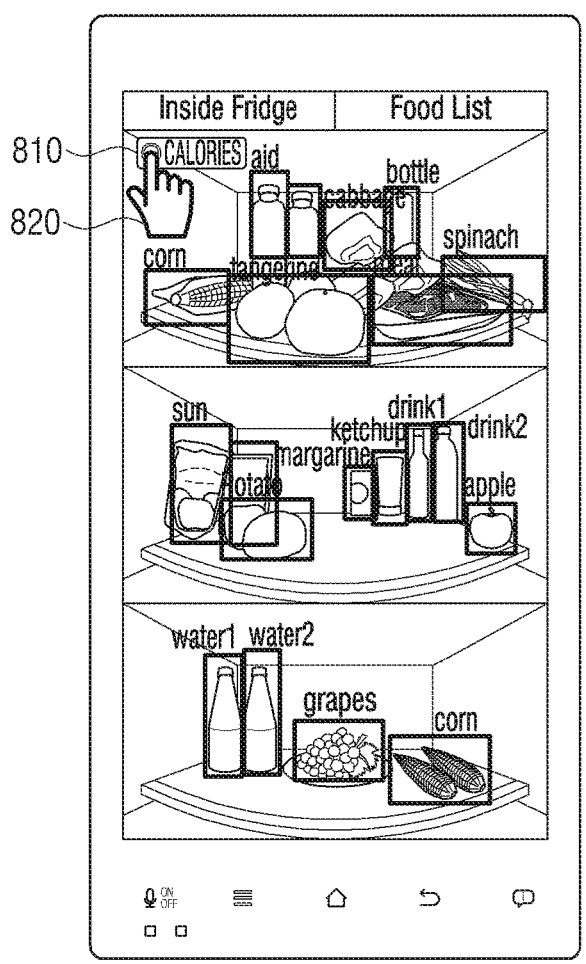
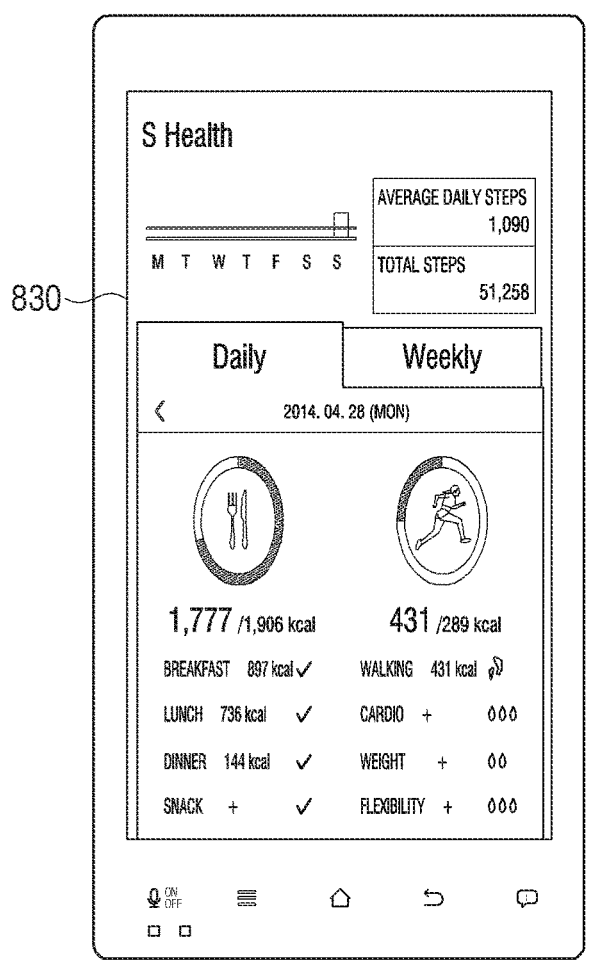

REFRIGERATOR, SERVER AND METHOD OF CONTROLLING THEREOF

CROSS-REFERENCE TO RELATED APPLICATION

This application is based on and claims priority under 35 U.S.C. § 119(a) of a Korean Patent Application number 10-2018-0069078, filed on Jun. 15, 2018, in the Korean Intellectual Property Office, and the disclosure of which is incorporated by reference herein in its entirety.

BACKGROUND

1. Field

The disclosure relates to a refrigerator, a server, and a method for recognizing food stored in the refrigerator by using the refrigerator and the server.

2. Description of Related Art

Refrigerator is an electronic apparatus (or home appliance) for stores food cool or frozen. A refrigerator may store not only food but also medicine, alcoholic liquor or cosmetics.

The advancement of technology has enabled an operation mode of the refrigerator to be displayed using a display. In addition, the refrigerator displays a user interface on the display to thereby display information or receive a user input. Further, recent refrigerators may include a communication interface connectable to an external apparatus (e.g., a server accessed to the Internet).

As such, the refrigerator has provided users with various services using the display and the communication interface.

The above information is presented as background information only to assist with an understanding of the disclosure. No determination has been made, and no assertion is made, as to whether any of the above might be applicable as prior art with regard to the disclosure.

SUMMARY

Provided are a refrigerator, a server, and a method of controlling thereof.

Additional aspects will be set forth in part in the description which follows and, in part, will be apparent from the description, or may be learned by practice of the presented embodiments.

In accordance with an aspect of the disclosure, a server includes a memory storing one or more instructions and at least one processor configured to execute the instructions to obtain at least one inside-fridge image captured in a refrigerator, by comparing a pre-stored image to the obtained at least one inside-fridge image, identify whether a change area in which a change occurred in the obtained at least one inside-fridge image is present in the obtained at least one inside-fridge image, based on the change area being not present in the obtained at least one inside-fridge image, obtain first food storage information, using a first result of recognizing the pre-stored image, based on the change area being present in the obtained at least one inside-fridge image, obtain second food storage information, using the obtained first food storage information and a second result of recognizing an object included in the obtained at least one inside-fridge image, and transmit, to the refrigerator, the obtained at least one inside-fridge image and either one or both of the obtained first food storage information and the obtained second food storage information.

The at least one processor is further configured to identify whether the change area is present in the obtained at least one inside-fridge image, based on a difference value between a first value of each of first pixels included in the pre-stored image and a second value of each of second pixels included in the obtained at least one inside-fridge image.

The at least one processor is further configured to apply, to the obtained at least one inside-fridge image, either one or both of a first image correction processing to correct blurring of the obtained at least one inside-fridge image and a second image correction processing to increase a clarity of the obtained at least one inside-fridge image, and identify whether the change area is present in the acquired at least one inside-fridge image to which the either one or both of the first image correction processing and the second image correction processing are applied.

The at least one processor is further configured to identify the change area in the obtained at least one inside-fridge image using a food change sensing model, and wherein the food change sensing model is a data recognition model which is trained with a first image, a second image identical to the first image but further including a partial area with change, and location information with the change, as a data for learning.

The at least one processor is further configured to change the obtained at least one inside-fridge image to a new image emphasizing an edge component of the obtained at least one inside-fridge image, and based on the obtained at least one inside-fridge image being changed to the new image, recognize the object included in the new image, based on a shape of the object which is identified based on the edge component.

The at least one processor is further configured to, based on the change area being present in the obtained at least one inside-fridge image, recognize the object included in the obtained at least one inside-fridge image, in the change area.

The at least one processor is further configured to recognize a first category of food included in the obtained at least one inside-fridge image using a food recognition model, wherein the food recognition model is a first data recognition model which is trained with a food image including a food, a food category to which the food belongs, and information of a place where the food is located in the food image, as a first data for learning.

The at least one processor is further configured to, based on the object being recognized as a processed food, recognize a second category of processed food included in the obtained at least one inside-fridge image using a processed food recognition model, wherein the processed food recognition model is a second data recognition model which is trained with multiple images for a same processed food, a processed food category of the same processed food, and a brand name of the same processed food, as a second data for learning.

The obtained at least one inside-fridge image comprises a first inside-fridge image and a second inside-fridge image, and wherein the at least one processor is further configured to obtain a third result of recognizing another object included in the second inside-fridge image but not being recognized in the first inside-fridge image.

In accordance with an aspect of the disclosure, an refrigerator includes a camera configured to capture a storage room storing food, a communication interface, a processor; and a memory storing one or more instructions that cause the processor to control the camera to capture an inside-fridge image, based on an occurrence of a predetermined event, and control the communication interface to transmit the captured inside-fridge image, to a server, and receive, from the server, either one or both of first food storage information and second food storage information corresponding to the transmitted inside-fridge image.

The refrigerator may further include a display, and the one or more instructions further cause the processor to control the display to display the captured inside-fridge image, based on a first user input to select a food included in the inside-fridge image displayed on the display, control the display to display at least one candidate category to which the selected food belongs, and based on a second user input to select one of the displayed at least one candidate categories, identify the selected one of the candidate categories, as a category of the food.

The refrigerator may further include a display, and the one or more instructions may further cause the processor to control the display to display a recipe providing execution object, based on a user input to select the recipe providing execution object displayed on the display, control the communication interface to transmit a category of a food included in the captured inside-fridge image, to the server, and receive a recipe obtained by the server using the transmitted category, and control the display to display the received recipe.

The refrigerator may further include a display, and the one or more instructions further cause the processor to control the display to display a food purchase website link execution object, based on a user input to select the food purchase website link execution object displayed on the display, control the communication interface to access a food purchase website selling a food category corresponding to a food that is previously included in the captured inside-fridge image but not currently included in the captured inside-fridge image, and control the display to display the accessed food purchase website.

The refrigerator may further include a display, and the instructions may further cause the processor to control the display to display a health information displaying execution object, and based on a user input to select the health information displaying execution object displayed on the display, control the display to display health information of a user, using a calorie of a food that is previously included in the captured inside-fridge image but not currently included in the captured inside-fridge image.

In accordance with an aspect of the disclosure, a refrigerator comprises a camera configured to capture a storage room storing food, a communication interface, a processor and a memory storing one or more instructions that cause the processor to, based on an occurrence of a predetermined event, control the camera to capture an inside-fridge image, identify whether a change area in which a change occurred in the captured inside-fridge image is present in the captured inside-fridge image, by comparing a pre-stored image to the captured inside-fridge image, based on the change area being not present in the captured inside-fridge image, obtain first food storage information, using a first result of recognizing the pre-stored image, and based on the change area being present in the captured inside-fridge image, control the communication interface to transmit the captured inside-fridge image, to a server and receive, from the server, second food storage information obtained by the server using the first food storage information and a second result of recognizing an object included in the transmitted inside-fridge image.

The one or more instructions cause the processor to identify whether the change area is present in the captured inside-fridge image, based on a difference value between a first value of each of first pixels included in the pre-stored image and a second value of each of second pixels included in the captured inside-fridge image.

The one or more instructions cause the processor to apply, to the captured inside-fridge image, either one or both of a first image correction processing to correct blurring of the captured inside-fridge image and a second image correction processing to increase a clarity of the captured inside-fridge image, and identify whether the change area is present in the captured inside-fridge image to which the either one or both of the first image correction processing and the second image correction processing are applied.

The one or more instructions cause the processor to identify the change area in the captured inside-fridge image using a food change sensing model, and wherein the food change sensing model is a data recognition model which is trained with a first image, a second image identical to the first image but further including a partial area with change, and location information with the change, as a data for learning.

In accordance with an aspect of the disclosure, a method for controlling a server, the method includes acquiring at least one inside-fridge image that is captured in a refrigerator, determining whether a change area in which a change occurred in the acquired at least one inside-fridge image is present in the acquired at least one inside-fridge image, by comparing a pre-stored image and the acquired at least one inside-fridge image, based on the change area being determined to not be present in the acquired at least one inside-fridge image, acquiring first food storage information, using a first result of recognizing the pre-stored image, based on the change area being determined to be present in the acquired at least one inside-fridge image, acquiring second food storage information, using the acquired first food storage information and a second result of recognizing an object included in the acquired at least one inside-fridge image, and transmitting, to the refrigerator, the acquired at least one inside-fridge image and either one or both of the acquired first food storage information and the acquired second food storage information.

The method may further include applying the pre-stored image and the acquired at least one inside-fridge image to a food change sensing model that is set to identify the change area in the acquired at least one inside-fridge image, and the food change sensing model may be a data recognition model that is trained with a first image, a second image identical to the first image but further including a partial area with change, and location information with the change, as a data for learning.

The method may further include applying the acquired at least one inside-fridge image to a food recognition model that is set to recognize a first category of food included in the acquired at least one inside-fridge image, and the food recognition model may be a first data recognition model that is trained with a food image including a food, a food category to which the food belongs, and information of a place where the food is located in the food image, as a first data for learning.

The method may further include, based on the object being recognized as a processed food, applying the acquired at least one inside-fridge image to a processed food recognition model that is set to recognize a second category of processed food included in the acquired at least one inside-fridge image, and the processed food recognition model may be a second data recognition model that is trained with multiple images for a same processed food, a processed food category of the same processed food, and a brand name of the same processed food, as a second data for learning.

In accordance with an aspect of the disclosure, a non-transitory computer-readable medium configured to store one or more computer programs including instructions that, when executed by a processor of an electronic apparatus, cause the electronic apparatus to acquire at least one inside-fridge image that is captured in a refrigerator, determine whether a change area in which a change occurred in the acquired at least one inside-fridge image is present in the acquired at least one inside-fridge image, by comparing a pre-stored image and the acquired at least one inside-fridge image, based on the change area being determined to not be present in the acquired at least one inside-fridge image, acquire first food storage information, using a first result of recognizing the pre-stored image, based on the change area being determined to be present in the acquired at least one inside-fridge image, acquire second food storage information, using the acquired first food storage information and a second result of recognizing an object included in the acquired at least one inside-fridge image, and transmit, to the refrigerator, the acquired at least one inside-fridge image and either one or both of the acquired first food storage information and the acquired second food storage information.

In accordance with an aspect of the disclosure, a refrigerator includes a first camera, a second camera, a first storage room, a second storage room, a communication interface, a processor, and a memory configured to store one or more instructions that cause the processor to control the first camera to capture a first inside-fridge image of the first storage room, control the second camera to capture a second inside-fridge image of the second storage room, determine whether an area changes in each of the captured first inside-fridge image and the captured second inside-fridge image, by comparing a pre-stored image to a respective one of the captured first inside-fridge image and the captured second inside-fridge image, based on the area being determined to not change in the captured first inside-fridge image, acquire first food storage information, using a first result of recognizing the pre-stored image, and based on the area being determined to change in the captured second inside-fridge image, control the communication interface to transmit the captured second inside-fridge image, to a server, and receive, from the server, second food storage information that is acquired by the server using the first food storage information and a second result of recognizing an object included in the transmitted second inside-fridge image.

The one or more instructions may further cause the processor to, based on the area being determined to not change in the captured second inside-fridge image, acquire the first food storage information, and based on the area being determined to change in the captured first inside-fridge image, control the communication interface to transmit the captured first inside-fridge image, to the server, and receive, from the server, third food storage information that is acquired by the server using the first food storage information and a third result of recognizing another object included in the transmitted first inside-fridge image.

BRIEF DESCRIPTION OF THE DRAWINGS

The above and other aspects, and advantages of certain embodiments of the disclosure will be more apparent from the following description taken in conjunction with the accompanying drawings, in which:

FIGS. 8A and 8B are diagrams illustrating a situation in which health information is provided using a result of the food recognition method, according to embodiments;

DETAILED DESCRIPTION

Figure 1A:
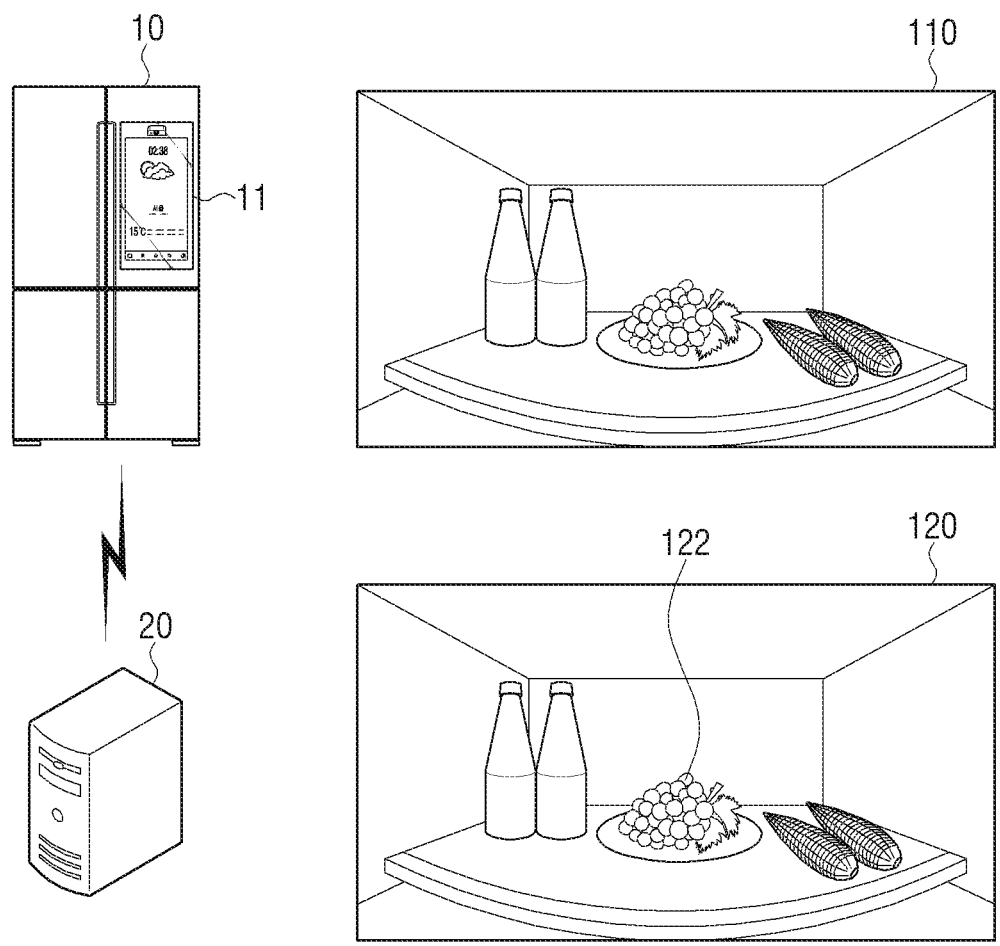
FIGS. 1A and 1B are diagrams provided to explain a food recognition method, according to embodiments.

Hereinafter, embodiments of the disclosure will be described with reference to the accompanying drawings. However, it may be understood that the disclosure is not limited to the embodiments described hereinafter, but includes various modifications, equivalents, and/or alternatives of the embodiments of the disclosure. In relation to explanation of the drawings, similar drawing reference numerals may be used for similar constituent elements.

In the description, the term "has," "may have," "includes" or "may include" indicates existence of a corresponding feature (e.g., a numerical value, a function, an operation, or a constituent element such as a component), but does not exclude existence of an additional feature.

In the description, the term "A or B," "at least one of A or/and B," or "one or more of A or/and B" may include all possible combinations of the items that are enumerated together. For example, the term "A or B" or "at least one of A or/and B" may designate (1) at least one A, (2) at least one B, or (3) both at least one A and at least one B.

In the description, the terms "first, second, and so forth" are used to describe diverse elements regardless of their order and/or importance and to discriminate one element from other elements, but are not limited to the corresponding elements. For example, a first user appliance and a second user appliance may indicate different user appliances regardless of their order or importance. For example, without departing from the scope as described herein, a first element may be referred to as a second element, or similarly, a second element may be referred to as a first element.

The term such as "module," "unit," "part," and so on is used to refer to an element that performs at least one function or operation, and such element may be implemented as hardware or software, or a combination of hardware and software. Further, except for when each of a plurality of "modules," "units," "parts," and the like needs to be realized in an individual hardware, the components may be integrated in at least one module or chip and be realized in at least one processor.

If it is described that an element (e.g., first element) is "operatively or communicatively coupled with/to" or is "connected to" another element (e.g., second element), it may be understood that the element may be connected to the other element directly or through still another element (e.g., third element). When it is mentioned that one element (e.g., first element) is "directly coupled" with or "directly connected to" another element (e.g., second element), it may be understood that there is no element (e.g., third element) present between the element and the other element.

The terms used in the description are used to describe an embodiment, but may not intend to limit the scope of other embodiments. Unless otherwise defined specifically, a singular expression may encompass a plural expression. All terms (including technical and scientific terms) used in the description could be used as meanings commonly understood by those ordinary skilled in the art to which the disclosure belongs. The terms that are used in the disclosure and are defined in a general dictionary may be used as meanings that are identical or similar to the meanings of the terms from the context of the related art, and they are not interpreted ideally or excessively unless they have been clearly and specially defined. According to circumstances, even the terms defined in the embodiments of the disclosure may not be interpreted as excluding the embodiments of the disclosure.

One of methods for using a display included in a refrigerator may be displaying food stored in the refrigerator on the display. For example, the refrigerator may display an image acquired using a camera capturing a storage room of the refrigerator, on the display, recognize food included in the image and display a name of the food, etc., on the display, together with the image.

The camera may capture the storage room to recognize the food included in the image generated by capturing the storage room, and thus a food recognition is performed every time that an inside-fridge image is generated, which is inconvenient. In addition, there may be a situation in which it is impossible to accurately recognize food placed as being overlapped in the refrigerator.

Accordingly, there is a demand for a method for maintaining efficiency of food recognition and recognizing food that is disposed as being overlapped in the refrigerator.

Figure 1B:
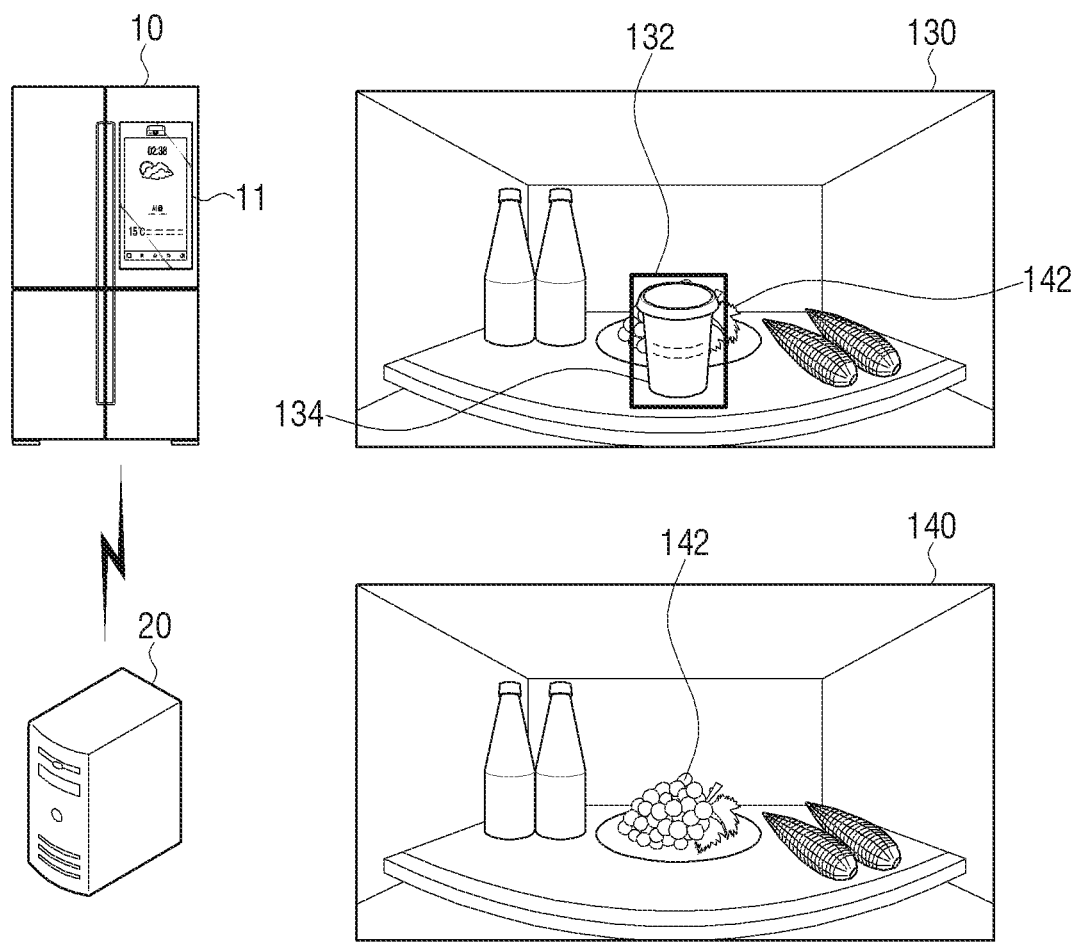

FIGS. 1A and 1B are diagrams provided to explain a food recognition method, according to embodiments.

In FIGS. 1A and 1B, the food recognition method may be executed in a server (or a cloud) 20 including one or more server, or may be executed in a refrigerator 10.

According to an embodiment, the refrigerator 10 and the server 20 may establish a communication network by using a wired or wireless communication method. The refrigerator 10 and the server 20 may include a wireless communication interface (e.g., a cellular communication module, a near-field wireless communication module, or a global navigation satellite system (GNSS) communication module) or a wired communication interface (e.g., a local area network (LAN) communication module, or a power line communication module), and may perform communication through a first network (e.g., a near-field communication network such as Bluetooth, Wi-Fi direct or infrared data association (IrDA)) or a second network (e.g., far-field communication network such as a cellular network, Internet, or a computer network (e.g., LAN or WAN)) by using the corresponding communication interface.

According to an embodiment, the refrigerator 10 may be a home appliance which includes a storage room for storing food, and a cooling air supplying apparatus for supplying a cooling air to the storage room, and which is capable of keeping food fresh. The refrigerator 10 may further include a camera. According to an embodiment, the refrigerator 10 may capture food stored in the storage room by using a camera and acquire an image.

According to an embodiment, the server 20 may include a plurality of servers including a first server, a second server, and a third server. For example, the first server may compare a plurality of images and identify a change area. The second server may, for example, identify food in an image. The third server may, for example, identify processed food.

According to the embodiments, the server 20 may further include a storage server for storing a plurality of images.

Hereinafter, it is assumed that a food recognition method is performed in the server 20.

In FIG. 1A, the server 20 may be in a state of pre-storing an image to be compared 120. In FIG. 1A, the refrigerator 10 may acquire an inside-fridge image 110.

According to an embodiment, the inside-fridge image 110 may be an image which is acquired using a camera included in the refrigerator 10. For example, the inside-fridge image 110 may be an image generated by capturing a storage room inside the refrigerator by using the camera included in the refrigerator.

According to an embodiment, the image to be compared 120 may be an image which is recognized by receiving, in the server 20, an inside-fridge image from the refrigerator 10 and detecting an object included in the inside-fridge image. That is, the image to be compared 120 may be an image which is acquired by the camera in the refrigerator 10 before the inside-fridge image 110 of FIG. 1A is acquired, transferred to the server 20, and recognized by the server 20 and stored.

According to an embodiment, when sensing occurrence of an event, the refrigerator 10 may acquire at least one inside-fridge image. For example, when an event that a door is opened and then closed occurs, the refrigerator 10 may acquire at least one inside-fridge image. However, the example is not limited thereto. For example, the refrigerator 10 may capture at least one inside-fridge image according to predetermined cycles, or may sense that a person is positioned in front of the refrigerator 10 and capture at least one inside-fridge image.

According to an embodiment, the refrigerator 10 may transmit the acquired at least one inside-fridge image 110 to the server 20.

The server 20 may identify a change area in which a change has occurred by contrasting the pre-stored image to be compared 120 with the inside-fridge image 110. For example, the server 20 may change the image to be compared 120 and the inside-fridge image 110 to an image emphasizing an edge component, and then compare the acquired shapes of the objects on the basis of the edge component and identify the change area.

According to an embodiment, the server 20 may identify the change area by using a pixel difference value. For example, the server 20 may calculate the respective differences between a red pixel value (R), green pixel value (G)

and blue pixel value (B) included in the image to be compared 120 and R, G and B values of the inside-fridge image 110, and identify the change area.

According to an embodiment, the server 20 may identify the change area by using an artificial intelligence algorithm. For example, the server 20 may apply at least one inside-fridge image 110 to a food change sensing model which is trained with an image, an image which is identical to the image but includes at least some parts with change, and information about locations with change as data for learning, and compare the food change sensing model to which the at least one inside-fridge image 110 is applied with the image to be compared 120. Thereby, the server 20 may identify the change area in the inside-fridge image 110.

Referring to FIG. 1A, upon identification, when a change area is not present in the inside-fridge image, the server 20 may transmit first food storage information which is a result of recognizing the pre-stored image to be compared, and the inside-fridge 110 to the refrigerator. The first food storage information may be, for example, information generated using a result of sensing an object in the image to be compared 120. In addition, the first food storage information may include, for example, any one or any combination of location information of food sensed in the image 120 to be compared, information about a food category to which a food belongs, information about a category of processed food to which a processed food belongs, and a brand name of a processed food.

Referring to FIG. 1A, the server 20 may not acquire a change area in which a change has occurred by comparing the inside-fridge image 110 with the image 120 to be compared. Accordingly, the server 20 may acquire the first food storage information as information to be sent to the refrigerator 10. The server 20 may, for example, transmit grapes as food category information and information about a location of grapes 122 in the image to be compared 120 to the refrigerator 10 as the first food storage information. In addition, the server 20 may transmit the inside-fridge image 110 received from the refrigerator 10 to the refrigerator 110.

According to the embodiments, the server 20 may perform an image correction processing for the inside-fridge image 110 received from the refrigerator 10, and then transmit, to the refrigerator 10, the inside-fridge image 110 for which the image correction processing is performed. The server 20 may perform an image processing to correct blurring that occurred when capturing is performed by the camera. For example, the server 20 may correct blurring by using a cross-correction algorithm between the previous image and the current image.

According to the embodiments, the server 20 may apply an image processing to enhance clarity of an opaque image that has occurred due to condensation, etc. to the inside-fridge image 110.

By performing the image processing, the server may detect an object at a high precision from the inside-fridge image 110. The refrigerator 10 may, always or selectively, receive the inside-fridge image 110 corrected by the server 20 and display the received inside-fridge image on a display 11.

According to an embodiment, the server 20 may correct the inside-fridge image by using an artificial intelligence model. For example, the server 20 may acquire an image from which condensation is eliminated by applying at least one inside-fridge image 110 to a food change sensing model which is trained with an image, an image for which a condensation effect is added to the image, and an image expressing only a condensation effect as a data for learning.

According to an embodiment, the refrigerator 10 may display the inside-fridge image 110 received from the server and the first food storage information on the display 11.

In FIG. 1B, the server 20 may be in a state of pre-storing the image to be compared 140. In FIG. 1B, the refrigerator 10 may acquire an inside-fridge image 130.

As described with reference to FIG. 1A, when an event (e.g., an event in which a door is opened and then closed) occurs, the refrigerator 10 may acquire at least one inside-fridge image 130.

According to an embodiment, the refrigerator 10 may transmit the at least one inside-fridge image 130 to the server 20. The server 20 may identify a change area in which a change has occurred by contrasting a pre-stored image to be compared 140 with the inside-fridge image 130.

For example, the server 20 may compare the inside-fridge image 130 with the image to be compared 140 using the change area identification methods described with reference to FIG. 1A, and sense that an object 134 is added to the inside-fridge image 130 and identify a change area 132.

According to an embodiment, as a result of identification, when a change area is present in the inside-fridge image, the server 20 may transmit second food storage information acquired using a result of recognizing an object included in the inside-fridge image 130 and the first food storage information, and the inside-fridge image 130 to the refrigerator.

According to an embodiment, the server 20 may change the image to be compared 140 and the inside-fridge image 130 to an image emphasizing an edge component, then find a shape of an acquired object based on the edge component, and compare the shape of the object with a data stored in the server 20 and recognize a food category to which the object belongs. The food category may be, for example, a name capable of representing a similar food.

According to an embodiment, when the object is recognized as a processed food, the server 20 may recognize a category of processed food to which the processed food belongs and/or a brand name of the processed food by using an additional processed food data additionally stored in the server 20.

According to an embodiment, the server 20 may sense the object by using an artificial intelligence algorithm, and recognize a food category to which the sensed object belongs. For example, the server 20 may sense the object by applying the inside-fridge image 130 to a food recognition model which is trained with an image in which food is present, a food category to which the food belongs, and information about a place where the food is located in the image as a data for learning, and may recognize a food category to which the object belongs.

According to an embodiment, as a result of recognizing the object by using a food identification model, when the object is recognized as a processed food, the server 20 may recognize a category of processed food to which the object belongs and/or a brand name of the processed food by using a processed food recognition model. For example, the server 20 may recognize a category of processed foods detected in the inside-fridge image 130 and/or a brand name of processed foods in the processed food database by using a processed food recognition model which is trained based on image similarity with multiple images for the same processed food, a category of processed food, and a brand name of processed food as a data for learning. The processed food database may be, for example, a database in which a category of processed food and a brand name of processed food are stored using images of various processed foods.

Referring to FIG. 1B, the server 20 may sense and recognize the object 134 added to the inside-fridge image 130. For example, the server 20 may sense and recognize a coffee drink as category information of the object 134 added to the inside-fridge image 130. In addition, the server 20 may acquire information about a place where the coffee drink 134 is located in the inside-fridge image 130.

According to the embodiments, when sensing an object in an inside-fridge image, the server 20 may sense the object only in a change area. For example, the server 20 may sense and recognize the object only in the changed area 132. For this reason, the server 20 may reduce a data processing load as compared with sensing and recognizing the object for the entire area of the inside-fridge image 130.

As described above, the server 20 may recognize the object in the inside-fridge image, and further acquire second food storage information by using the first food storage information.

According to an embodiment, the server 20 may identify the presence of an object 142 covered by the coffee drink 134 in the inside-fridge image 130. The server 20 may acquire information about the objects sensed in the first food storage information and location information of the respective objects. For example, the server 20 may identify the presence of grapes at a place where an object 142 is placed in the image to be compared 140.

As described above, the server 20 may acquire the second food storage information by using a result of detecting a new object in the inside-fridge image 130 (e.g., information that a coffee drink is added) and information acquired from the first food storage information (e.g., information that grapes are present at a place where the coffee drink is disposed). The server 20 may transmit the acquired second food storage information and the inside-fridge image 130 to the refrigerator 10.

According to an embodiment, the refrigerator 10 may display the inside-fridge image 130 received from the server and the second food storage information on the display 11.

According to the embodiments, the refrigerator 10 may include a plurality of cameras. For example, the refrigerator 10 may include a first camera for capturing a first storage room, and a second camera for capturing a second storage room. However, the example is not limited thereto. For example, the refrigerator 10 may include the number of cameras corresponding to the number of storage rooms included in the refrigerator 10.

The refrigerator 10 may acquire a first inside-fridge image and a second inside-fridge image by using the first camera and the second camera. The refrigerator 10 may transmit the first inside-fridge image and the second inside-fridge image to the server 20. The server 20 may identify a change area for the first inside-fridge image and the second inside-fridge image by using the process described with reference to FIGS. 1A and 1B.

For example, in a case that a change area is not present in the first inside-fridge image, with respect to the first storage room, the server 20 may transmit 1-1 food storage information (e.g., information acquired using an object included in the first image to be compared) and the first inside-fridge image to the refrigerator. In addition, in a case that a change area is present in the second inside-fridge image, with respect to the second storage room, the server 20 may transmit 2-2 food storage information acquired using a result of recognizing an object included in an object included in the second inside-fridge image and 1-2 food storage information (e.g., information acquired using an object included in the second image to be compared), and the second inside-fridge image to the refrigerator.

As such, the food recognition method according to an embodiment may, according to an identification result from comparing a pre-stored image to be compared with a newly-acquired inside-fridge image, use a previously-stored data or may simultaneously use a data acquired from the newly-acquired inside-fridge image and the previously-stored data. Thereby, it is possible to increase a recognition rate of an object included in an inside-fridge image, and to reduce a load of the server 20.

Figure 2A:
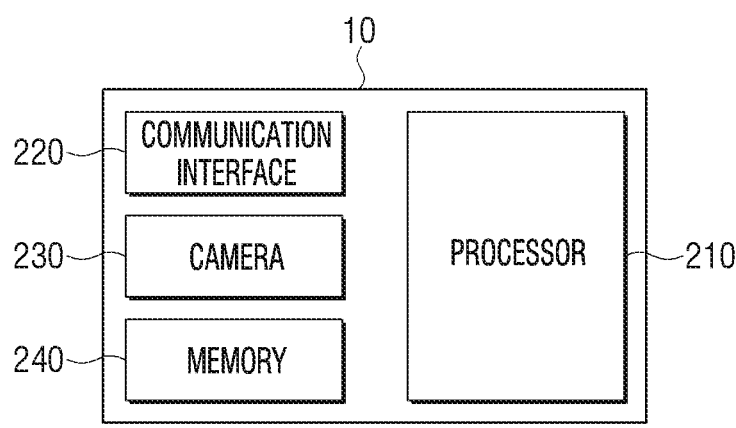
FIGS. 2A and 2B are block diagrams of a brief configuration of a refrigerator and a server, according to an embodiment.
Figure 2B:
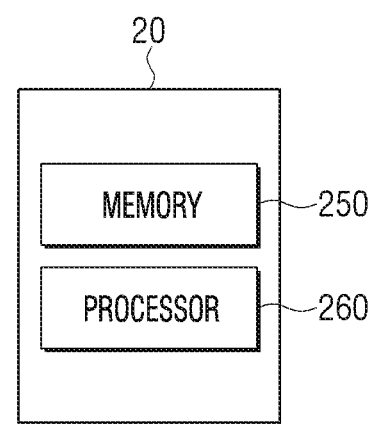

FIGS. 2A and 2B are block diagrams of a brief configuration of a refrigerator and a server, according to an embodiment.

Referring to FIG. 2A, the refrigerator 10 according to an embodiment may include a processor 210, a communication interface 220, a camera 230, and a memory 240. However, embodiments are not limited to any specific examples. For example, the refrigerator 10 may include further elements, or may not include some elements.

According to an embodiment, the processor 210 may control the overall operation of the refrigerator 10. For example, the processor 210 may receive a user input via the communication interface 220. The processor 210 may control the memory 240 to execute a stored program, and call or store information.

According to an embodiment, in a case that a predetermined event occurs, the processor 210 may control the camera 230 to capture at least one inside-fridge image. The processor 210 may contrast a pre-stored image to be compared with an inside-fridge image and identify a change area in which a change has occurred. In a case that a change area is not present in the inside-fridge image, the processor 210 may acquire first food storage information which is a result of recognizing the image to be compared. In a case that a change area is present in the inside-fridge image, the processor 210 may control the communication interface 220 to transmit the inside-fridge image to the server 20, and when the server 20 receiving the inside-fridge image acquires second food storage information using a result of recognizing an object in the inside-fridge image and the first food storage information, receive the acquired second food storage information from the server 20.

According to an embodiment, the communication interface 220 may be controlled by the processor 210 to connect the refrigerator 10 to an external apparatus. The communication interface 220 may include one of elements implementing various wired or wireless communication methods such as wireless LAN, Bluetooth, wired Ethernet, and the like, to correspond to a performance and structure of the refrigerator 10.

According to an embodiment, the memory 240 may include a storage medium of at least one type from among a memory (e.g., Secure Digital (SD) memory, XD memory, and the like) of a flash memory type, hard disk type, multimedia card micro type, and card type, a Random Access Memory (RAM), a Static Random Access Memory (SRAM), a Read-Only Memory (ROM), an Electrically Erasable Programmable Read-Only Memory (EEPROM), a Programmable Read-Only Memory (PROM), a magnetic memory, a magnetic disk, and an optic disk.

According to an embodiment, the memory 240 may, when a predetermined event occurs, control the camera 230 to capture at least one inside-fridge image, contrast a pre-stored image to be compared with an inside-fridge image and acquire a change area in which a change has occurred, when a change area is present in the inside-fridge image, acquire first food storage information, when a change area is present in an inside-fridge image, control the communication interface 220 to transmit the inside-fridge image to the server 20, and store instructions set to receive, in the server 20, food storage information acquired by the server 20 using a result of recognizing an object from the inside-fridge image and the first food storage information.

According to an embodiment, the camera 230 may be included in the refrigerator 10, and capture a storage room of the refrigerator 10. However, the example is not limited thereto. For example, the camera 230 may capture a storage room within the refrigerator 10, and the outside of the refrigerator 10. The camera 230 may include a first camera, a second camera, or a third camera. For example, the first camera may capture a first storage room. The second camera may capture a second storage room, and the third camera may capture a third storage room.

According to the embodiments, the camera 230 may be provided on a door of the refrigerator 10. However, embodiments are not limited to any specific examples.

Referring to FIG. 2B, the server 20 may include a memory 250 and a processor 260.

According to an embodiment, the processor 260 may acquire at least one inside-fridge image captured in the refrigerator. For example, the processor 260 may receive the at least one inside-fridge image from the refrigerator 10 through a communication interface or module.

According to an embodiment, the processor 260 may contrast a pre-stored image to be compared with an inside-fridge image and identify a change area in which a change has occurred.

According to an embodiment, when a change area is not present, the processor 260 may transmit the first food storage information which is a result of recognizing a pre-stored image to be compared, and the inside-fridge image to the refrigerator.

According to an embodiment, when a change area is present in the inside-fridge image, the processor 260 may acquire second food storage information using a result of recognizing an object included in the inside-fridge image, and the first food storage information, and the processor 260 may transmit the second food storage information and the inside-fridge image to the refrigerator.

Figure 3:
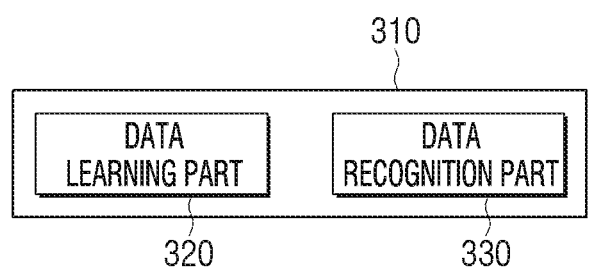
FIG. 3 is a block diagram of a processor, according to an embodiment.

FIG. 3 is a block diagram of a processor included in at least one of the refrigerator 10 or the server 20, according to an embodiment.

Referring to FIG. 3, a processor 310 according to the embodiments may include a data learning part 320 and a data recognition part 330. The processor 310 may include the processor 210 of FIG. 2A, and the data processing part 260 of FIG. 2B.

According to an embodiment, the data learning part 320 may train a food change sensing model to establish a criterion for identifying a change area in an image. The data learning part 320 may train the food change sensing model to establish a criterion regarding which learning data is to be used to identify the change area in the image or how to identify the change area in the image using the learning data.

According to an embodiment, the data learning part 320 the data learning part is a data for learning, which may train the food change sensing model by using an image, an image identical to the image but includes a change in at least some areas, and location information with change.

For example, the data for learning may be an image of a storage room with milk and an apple, an image to which a cucumber is added to the storage room, and information relating to a position to which the cucumber is added.

According to the embodiments, the data learning part 320 may train the food change sensing model to have a criterion for correcting an inside-fridge image. The data learning part 320 may train the food change sensing model to establish a criterion regarding which learning data is to be used to correct an image or how to correct the image using the learning data.

According to the embodiments, the data learning part 320 is a data for learning, which may train the food change sensing model by using an image, an image to which a condensation effect is added to the image, and an image in which only the condensation effect is expressed.

According to an embodiment, the data recognition part 330 may identify a change area in the image on the basis of various types of data for recognition. The data recognition part 330 may contrast at least one inside-fridge image input using the trained food change sensing model with the image to be compared, and identify the changed area.

According to an embodiment, the data recognition part 330 may use a result of identifying a change area in at least one inside-fridge image and a user response (or feedback) to the identification result to update the food change sensing model with the input at least one inside-fridge image and the image to be compared as input values of the food change sensing model. Accordingly, the food change sensing model may increase a probability to identify a change area in accordance with a user's tendency.

For example, in a case that an image to be compared including an orange and an apple and an inside-fridge image identical to the image but receiving input of an inside-fridge image including a melon are input, the data recognition part 330 may identify an area to which the melon is added from the image including the melon.

According to the embodiments, the data recognition part 330 may correct an image on the basis of various types of data for recognition. The data recognition part 330 may correct at least one inside-fridge image input using the trained food change sensing model.

According to the embodiments, the data recognition part 330 may use a result of correcting at least one inside-fridge image and a user response (or feedback) for the correction result to update the food change sensing model, with the input at least one inside-fridge image as an input value of the food change sensing model. Accordingly, the food change sensing model may correct the image in accordance with a user's tendency.

For example, in a case that an image with a banana in which a condensation has occurred is input as an inside-fridge image, the data recognition part 330 may correct the image to an image in which the banana is clearly visible by eliminating the condensation.

According to an embodiment, the data learning part 320 may train a food change sensing model to establish a criterion for detecting and recognizing a food category in the image. The data learning part 320 may train the food recognition model to establish a criterion regarding which learning data is to be used to detect and recognize (or identify) a food category in the image or how to detect and recognize the food category in the image using the learning data.

According to an embodiment, the data learning part 320 is a data for learning, which may train the food recognition model using an image with food, a food category to which the food belongs, and information about a place where the food is located in the image.

For example, the data for learning may be an image of a storage room with a cucumber and an apple, a category of food called "cucumber" and "apple" (e.g., the names of cucumber and apple), and information about locations of the cucumber and the apple in the image.

According to an embodiment, the data recognition part 330 may recognize a category of food included in the image on the basis of various types of data for recognition. The data recognition part 330 may, on the basis of an image input using the trained food recognition model, sense and recognize (or identify) a category of food included in the image.

According to an embodiment, the data recognition part 330 may use a result of recognizing a category of food included in the image and a user response to the recognition result to update the food recognition model with the input image as an input value of the food recognition model. Accordingly, the food recognition model may increase a probability to recognize an object in accordance with a user's tendency.

For example, in a case that an image including an orange and an apple is input, the data recognition part 330 may sense and recognize the orange and the apple and acquire food categories of "orange" and "apple" from the image.

According to an embodiment, the data learning part 320 may train a processed food recognition model to establish a criterion for find the same product image in the processed food database. The data learning part 320 may train the processed food recognition model to establish a criterion regarding which learning data is to be used to search for (or identify) a processed food in the image or how to search for and recognize the food in the image using the learning data.

According to an embodiment, the data learning part 320 is a data for learning, which may train a processed food search model using multiple images of a processed food, a category of processed food, and a brand name of processed food.

For example, the data for learning may be various types of images of milk, a category of processed food called "milk," and a brand name of each milk.

The data recognition part 330 may recognize a category of processed food included in the image on the basis of various types of data for recognition. The data recognition part 330 may, on the basis of an image input using the trained processed food recognition model, sense and recognize (or identify) a category of processed food included in the image.

According to an embodiment, the data recognition part 330 may use a result of recognizing a category of processed food included in the image and a user response to the recognition result to update the processed food recognition model with the input image as an input value of the processed food recognition model. Accordingly, the processed food recognition model may increase a probability to recognize an object in accordance with a user's tendency.

For example, in a case that an image including milk is input, the data recognition part 330 may sense and recognize milk and acquire a food category of "milk" and a brand name of milk from the image.

The food change sensing model, the food recognition model, and the processed food recognition model may be constructed in consideration of the application field of the recognition model, the purpose of learning, or the computer performance of the device. The food change sensing model, the food recognition model, and the processed food recognition model may be, for example, a neural network-based model. The food change sensing model, the food recognition model, and the processed food recognition model may include, for example, a neural network model or a deep learning model advanced from the neural network. A plurality of network nodes in the deep learning model may be positioned at different depths (or layers) from each other, and may exchange data according to a convolution connection relationship. For example, food change sensing models, food recognition models and processed food recognition models such as Deep Neural Network (DNN), Recurrent Neural Network (RNN), and Bidirectional Recurrent Deep Neural Network (BDNR) may be used, but are not limited thereto.

Either one or both of the data learning part 320 and the data recognition part 330 may be manufactured in the form of at least one hardware chip and mounted on the electronic apparatus. For example, either one or both of the data learning part 320 and the data recognition part 330 may be manufactured in the form of an exclusive hardware chip for artificial intelligence (AI), or may be manufactured as a portion of the previous general processor (e.g., CPU or application processor) or a graphic exclusive processor (e.g., GPU), and mounted in the various electronic apparatuses described above.

According to an embodiment, the exclusive hardware chip for artificial intelligence may be an exclusive processor which is specialized in probability operation, and may show a higher performance compared with the previous general processor to facilitate processing of a computing operation in the field of artificial intelligence such as machine learning.

The data learning part 320 and the data recognizing part 330 may be mounted on one electronic apparatus or on separate electronic apparatuses, respectively. For example, one of the data learning part 320 and the data recognition part 330 may be included in the refrigerator 10, and the other one may be included in the server 20. In addition, one of the data learning part 320 and the data recognition part 330 may be included in a first server, and the other one may be included in a second server which is different from the first server. The data learning part 320 and the data recognition part 330 may provide information about the food change sensing model, the food recognition model, and the processed food recognition model constructed by the data learning part 320 to the data recognition part 330 or the data input to the data recognition part 330 may be provided to the data learning part 320 as additional learning data via wire or wirelessly.

Either one or both of the data learning part 320 and the data recognition part 330 may be implemented as a software module. When either one or both of the data learning part 320 and the data recognition part 330 is implemented as a software module (or a program module including an instruction), the software module may be stored in non-transitory computer readable media. Further, in this case, at least one software module may be provided by an operating system (OS) or by a predetermined application. Alternatively, part of at least one of the at least one software module may be provided by an operating system (OS), and some of the at least one software module may be provided by a predetermined application.

Figure 4A:
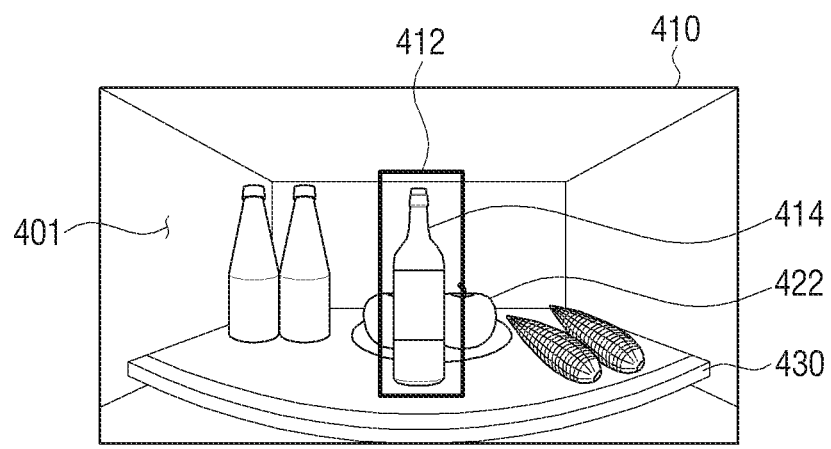
FIGS. 4A and 4B are diagrams illustrating a situation in which a plurality of cameras are used in the food recognition method, according to embodiments.
Figure 4B:
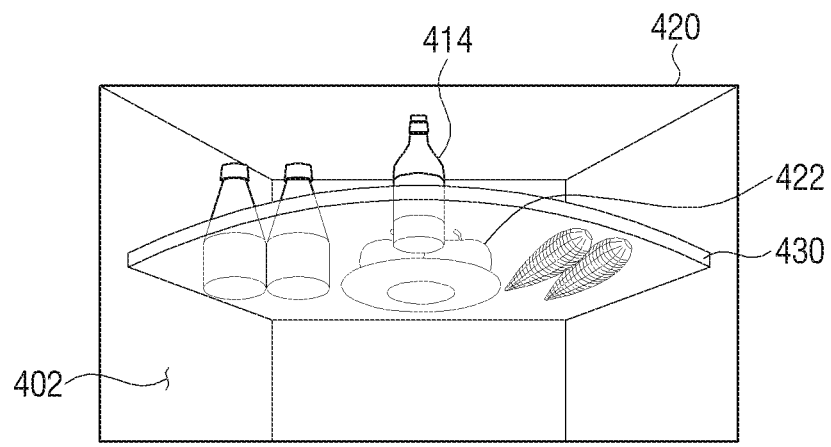

FIGS. 4A and 4B are diagrams illustrating a situation in which a plurality of cameras are used in the food recognition method, according to embodiments.

According to the embodiments, the refrigerator 10 may include a plurality of cameras for capturing a storage room. For example, the refrigerator 10 may include first and second cameras for capturing the storage room. The respective cameras may include a lens module capable of capturing a view angle of approximately 150 to 180 degrees. An example position at which the cameras are provided will be described with reference to FIG. 13.

According to an embodiment, the first camera may capture a first storage room 401, and the second camera may capture a second storage room 402 positioned below the first storage room. According to the embodiments, a shelf 430 between the first storage room 401 and the second storage room 402 may be of a transparent glass or plastic material.

FIG. 4A is a first inside-fridge image 410. The first inside-fridge image 410 may be, for example, an image for which the first storage room 401 is captured using the first camera. FIG. 4B is a partial area of a second inside-fridge image 420. The second inside-fridge image 420 may be, for example, an image for which the second storage room 402 is captured using the second camera. For example, FIG. 4B may be a partial area of the second inside-fridge image 420 indicating an area in which the first storage room 401 is visible through the transparent shelf 430 from among the second inside-fridge image 420 acquired by the second camera.

Referring to FIG. 4A, the server 20 is in a state of identifying a change area 412 in the first inside-fridge image 410. For example, the server 20 may identify the change area in the first inside-fridge image 410 using the first inside-fridge image 410 and a pre-stored first image to be compared.

According to the embodiments, the refrigerator 10 may identify the change area in the first inside-fridge image 410. For example, the server 20 may identify the change area in the first inside-fridge image 410 using the first inside-fridge image 410 acquired using the camera and the first image to be compared pre-stored in the refrigerator 10. In this case, the first image to be compared may be an image which is captured using the first camera and transferred to the server in which a food is detected, recognized, and then transferred to the refrigerator 10.

As described above with reference to FIG. 1B, in a case that a change area in an inside-fridge image is acquired, the server 20 may transfer the second food storage information acquired using a result of recognizing an object included in the inside-fridge image and the first food storage information, and the inside-fridge image to the refrigerator.

According to the embodiments, in a case that the server 20 stores a plurality of inside-fridge images, the server 20 may recognize the object included in the inside-fridge image using the plurality of inside-fridge images. That is, when the object included in the first inside-fridge image is recognized, the second inside-fridge image may be used.

For example, the server 20 may sense and recognize a wine bottle 414 as category information of processed food in the first inside-fridge image 410. The server 20 may identify the presence of an object 422 covered by the wine bottle 414 in the first inside-fridge image.

The server 20 may sense and recognize the object 422 in the second inside-fridge image 420. For example, the server 20 may sense and recognize the wine bottle 414 and the apple 422 in the second inside-fridge image 420. The server 20 may identify that the wine bottle 414 and the apple 422 are food or processed food stored in the first storage room 401 based on the fact that the wine bottle 414 and the apple 422 are recognized on the upper side of the second inside-fridge image 420. Alternatively, the server 20 may identify the shelf 430, and identify that the wine bottle 414 may identify that the wine bottle 414 and the apple 422 are food stored in the first storage room 401 based on the fact that the wine 414 and the apple 422 are placed on the shelf 430.

According to an embodiment, the server 20 may recognize that the object 422 placed behind the wine bottle 414 in the first inside-fridge image 410 based on a result of recognizing the apple 422 in the second inside-fridge image 420.

Accordingly, it is possible to recognize food hidden by another food by combining a plurality of inside-fridge images.

Figure 5A:
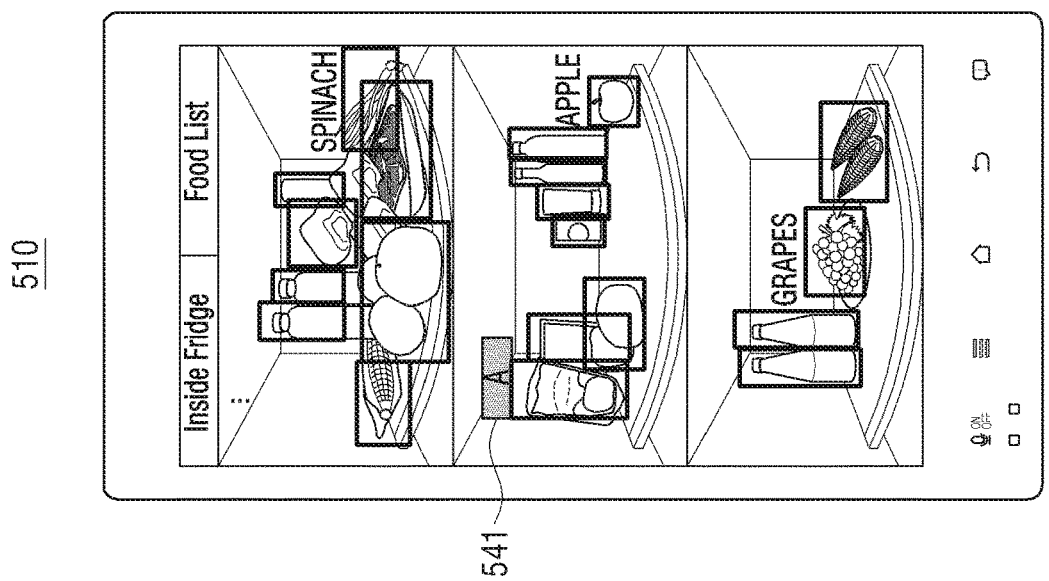
FIGS. 5A, 5B and 5C are diagrams illustrating a situation in which a category of food is determined using a result of the food recognition method, according to embodiments.
Figure 5B:
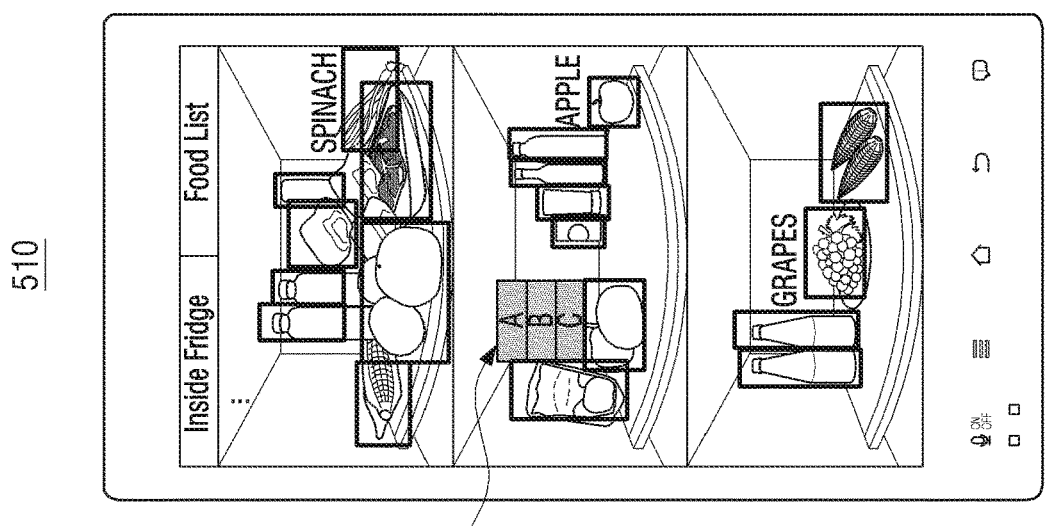
Figure 5C:
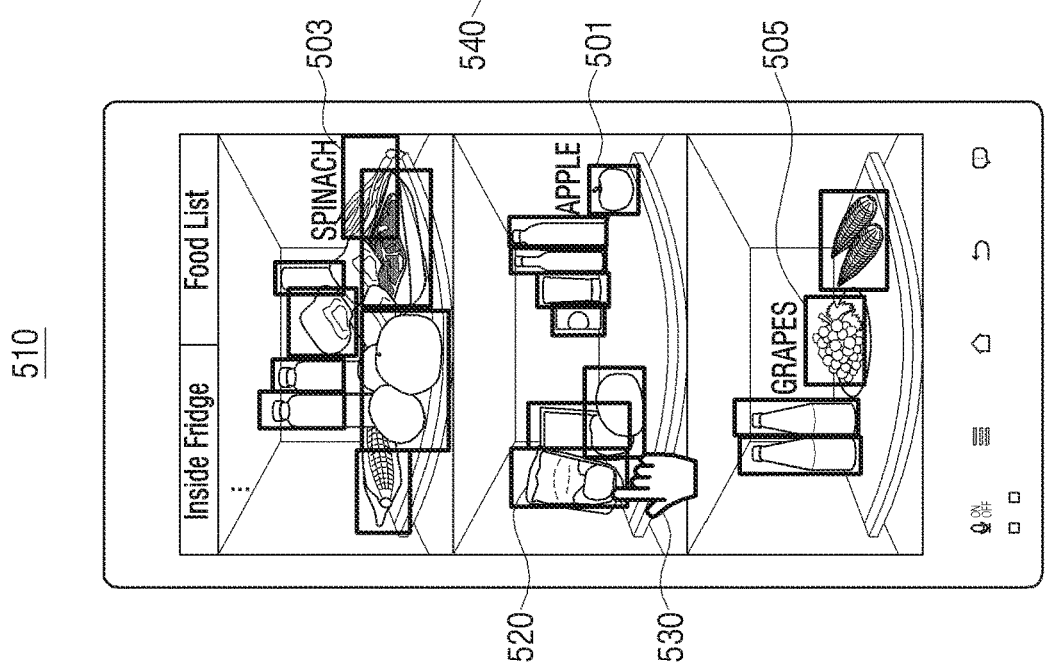

FIGS. 5A, 5B and 5C are diagrams illustrating a situation in which a category of food is determined using a result of the food recognition method, according to embodiments.

Referring to FIG. 5A, the refrigerator 10 may display, on a display 510, food stored in the refrigerator 10 based on the acquired at least one inside-fridge image and food storage information. The display 510 may include the display 10 of FIG. 1A.

According to an embodiment, the refrigerator 10 may display, on the display 510, a food together with a food category recognized using the food recognition method. For example, with respect to an apple 501, spinach 503 and grapes 505 of which the categories are identified, the refrigerator 10 may display categories "apple," "spinach" and "grapes" adjacently to the respective foods.

According to the embodiments, the refrigerator 10 may provide a candidate category in which the recognized foods may be included, using the food recognition method.

Referring to FIG. 5A, the refrigerator 10 may receive a user input 530 to select one object 520 from among the foods displayed on the display 510.

Referring to FIG. 5B, the refrigerator 10 may display, on the display 510, candidate categories 540 in which the selected object 520 may be included. The candidate categories 540 may be, for example, as described with reference to FIG. 1B, categories that are recognized by sensing the object in an inside-fridge image by the server 20.

According to an embodiment, the refrigerator 10 may receive a user input to select one of the candidate categories 540. That is, the user may determine and select a category to which the object 520 belongs from among the candidate categories 540 displayed on the display 510.

Referring to FIG. 5C, the refrigerator 10 may determine a category 541 input by the user as a category of the detected object 520, and display the determined category on the display 510.

According to an embodiment, the category 541 for the object 520 selected by the user may be used as a data for learning. For example, the refrigerator 10 may transmit the object 520 the category 541 selected by the user for the object 520 to the server 20. The server 20 may apply the received data the data learning part 320 as a data for learning. The data learning part 320 may train a food recognition model by using the received data. As the number that a data generated by a user feedback is used as a data for learning of the food recognition model increases, the possibility that the food recognition model recognizes the object in accordance with a user tendency may be increased.

Figure 6A:
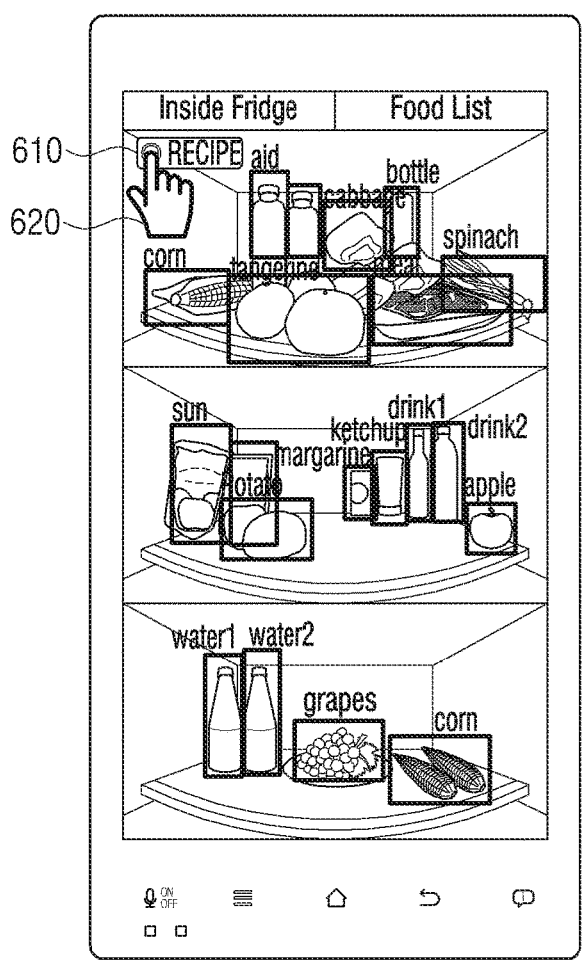
FIGS. 6A and 6B are diagrams illustrating a situation in which a recipe is acquired using a result of the food recognition method, according to embodiments.
Figure 6B:
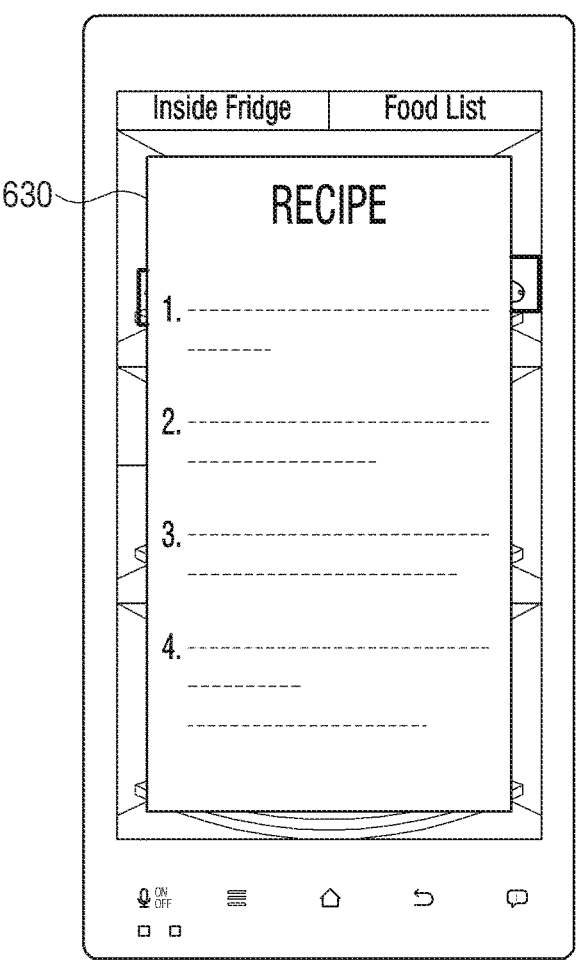

FIGS. 6A and 6B are diagrams illustrating a situation in which a recipe is acquired using a result of the food recognition method, according to embodiments.

Referring to FIG. 6A, the refrigerator 10 may display, on the display 510, food stored in the refrigerator 10 based on the acquired at least one inside-fridge image. The refrigerator 10 may display, on the display 510, a food together with a food category recognized using the food recognition method.

According to an embodiment, the refrigerator 10 may provide a recipe by using a category of the recognized food.

Referring to FIG. 6A, the refrigerator 10 may display an execution object 610 providing a recipe to the display 510. The refrigerator 10 may receive a user input 620 to select the execution object 610 providing the recipe.

Referring to FIG. 6B, the refrigerator 10 may display, on the display 510, a recipe 630 for food that may be prepared using a stored food, according to the user input to select the execution object 620.

For example, the refrigerator 10 may transmit a category of food stored in the server providing the recipe, and receive the recipe 630 acquired by the server using the received food category and display the received recipe on the display 510.

According to the embodiments, the refrigerator 10 may set priority for a food category and transmit the set priority to the server. For example, the refrigerator 10 may set high priority for food categories of which the dates for which the foods are stored in the refrigerator 10 are the oldest. Accordingly, the refrigerator 10 may first provide users with food with older shelf life.

According to the embodiments, the refrigerator 10 may store various recipes in a memory (e.g., the memory 240 of FIG. 2). In this case, the refrigerator 10 may display, on the display 510, the recipe 630 for a food that may be prepared using the food category received from the server 20, according to a user request.

Figure 7A:
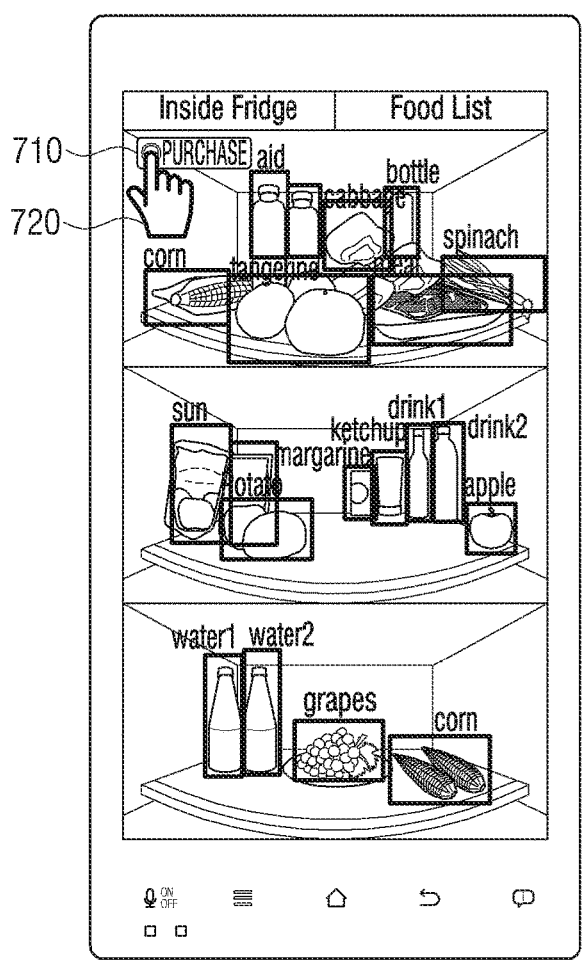
FIGS. 7A and 7B are diagrams illustrating a situation in which an article is purchased using a result of the food recognition method, according to embodiments.
Figure 7B:
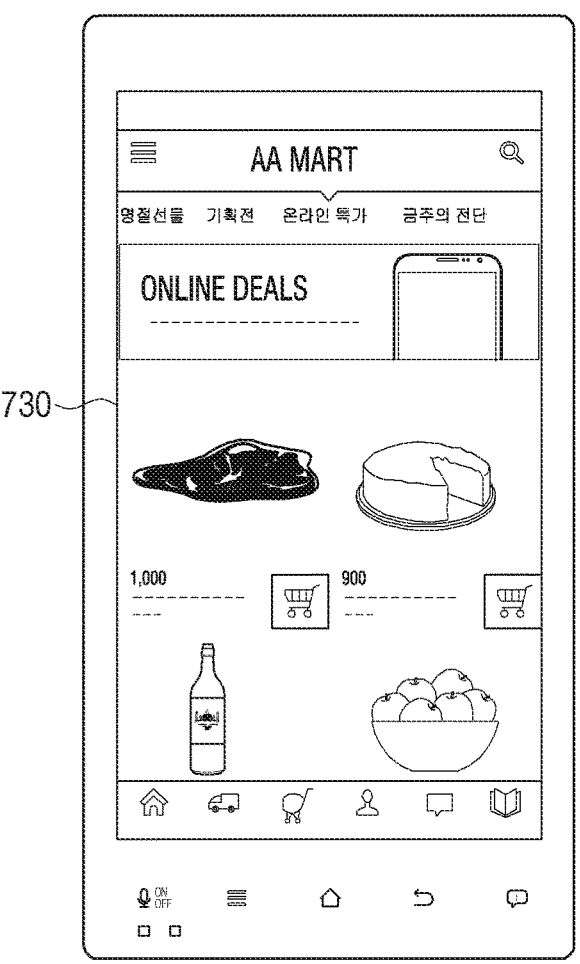

FIGS. 7A and 7B are diagrams illustrating a situation in which an article is purchased using a result of the food recognition method, according to embodiments.

Referring to FIG. 7A, the refrigerator 10 may display, on the display 510, food stored in the refrigerator 10 based on the acquired at least one inside-fridge image. The refrigerator 10 may display, on the display 510, a food together with a food category recognized using the food recognition method.

According to an embodiment, the refrigerator 10 may provide a guidance to food purchase using the recognized food category.

Referring to FIG. 7A, the refrigerator 10 may display, on the display 510, an execution object 710 linked to a food purchase website. The refrigerator 10 may receive a user input 720 to select the execution object 710 linked to the food purchase website.

Referring to FIG. 7B, the refrigerator 10 may display, on the display 510, a food purchase website 730 according to the user input 720 to select the execution object 710.

For example, the refrigerator 10 may access a food purchase website which sells a food category corresponding to a food having been previously stored in the refrigerator 10 but is not currently stored in the refrigerator 10. Alternatively, the refrigerator 10 may access a food purchase website selling a category of a food appropriate for a current season using weather information.

According to the embodiments, the refrigerator 10 may access a food purchase website identifying a food used in a recipe frequently selected by the user but not currently stored in the refrigerator 10, and selling a food included in the identified category, using information of foods used in the recipe displayed on the display 510 of FIG. 6.

FIGS. 8A and 8B are diagrams illustrating a situation in which health information is provided using a result of the food recognition method, according to embodiments.

Referring to FIG. 8A, the refrigerator 10 may display, on the display 510, food stored in the refrigerator 10 based on the acquired at least one inside-fridge image. The refrigerator 10 may display, on the display 510, a food together with a food category recognized using the food recognition method.

According to an embodiment, the refrigerator 10 may provide a guidance as to health information of the user using the recognized food category.

Referring to FIG. 8A, the refrigerator 10 may display an execution object 810 displaying the health information on the display 510. The refrigerator 10 may receive a user input 820 to select the execution object 810 displaying the health information.

Referring to FIG. 8B, the refrigerator 10 may display health information 830 on the display 510 according to the user input to select the execution object 810.

For example, the refrigerator 10 may store calories included in a food stored in the refrigerator 10. The refrigerator 10 may estimate a caloric intake of the user according to a situation in which food is reduced or gone, and provide the estimated calories as health information.

According to the embodiments, the refrigerator 10 may estimate calorie intake of the user in breakfast, lunch and dinner using a time at which food is reduced or gone, and provide the estimated calories as health information. Alternatively, the refrigerator 10 may estimate a user intake of calories for a week period or a month period using a time at which food is reduced or gone, and provide the estimated calories as health information.

According to the embodiments, the refrigerator 10 may receive information about an amount of exercise of the user from a personal device or wearable device capable of measuring the exercise amount. The refrigerator 10 may include the received exercise amount information (e.g., calories consumed, etc.) in the health information 830, and provide the health information.

In FIGS. 5-8, it is assumed that the display 510 included in the refrigerator 10 is used, but the example is not limited thereto. For example, the server 20 may transmit first food storage information or second food storage information to another electronic apparatus (e.g., smartphone, etc.) instead of the refrigerator 10. In this case, the user may perform the operation described in FIGS. 5-8 using a display included in the other electronic apparatus.

Figure 9A:
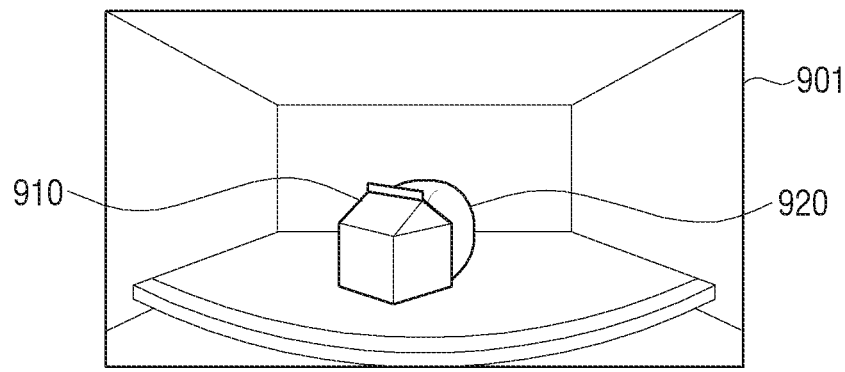
FIGS. 9A, 9B and 9C are diagrams illustrating a food recognition method, according to embodiments.
Figure 9B:
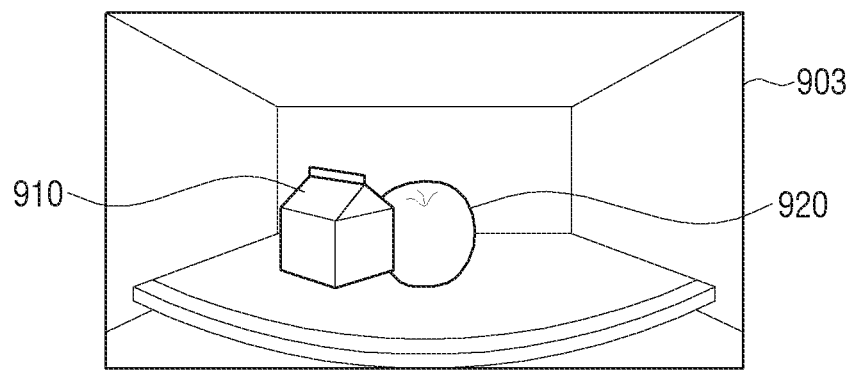
Figure 9C:
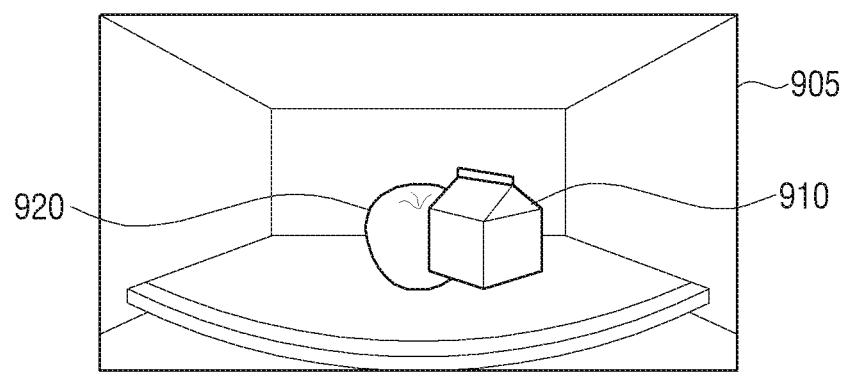

FIGS. 9A, 9B and 9C are diagrams illustrating a food recognition method, according to embodiments.

Referring to FIGS. 9A to 9C, the refrigerator 10 may increase performance of recognizing a food category using inside-fridge images acquired continuously.

Referring to FIG. 9A, the refrigerator 10 may acquire an inside-fridge image 901 at a t time point. For example, the refrigerator 10 may acquire the inside-fridge image 901 at the t time point while the door is opened. The refrigerator 10 may transmit the inside-fridge image 901 at the t time point to the server 20, and receive food storage information generated by recognizing food in the inside-fridge image 901 at the t time point by the server 20. However, the example is not limited thereto. For example, food storage information may be generated by recognizing food included in the inside-fridge image 901 at the t time point by using a processor (e.g., the processor 210 of FIG. 2) included in the refrigerator 10. In FIGS. 9A to 9C, it is assumed that a food is recognized by the refrigerator 10.

According to an embodiment, the refrigerator 10 may detect and recognize an object in the inside-fridge image 901 at the t time point. For example, the refrigerator 10 may detect a processed food category of milk 910. In this case, the refrigerator 10 may not detect an object placed behind the milk 910.

FIGS. 9B to 9C are images generated by capturing a state in which the milk 910 is moved by the user. For example, the refrigerator 10 may acquire an inside-fridge image 903 at a t+1 time point and an inside-fridge image 905 at a t+2 time point. The refrigerator 10 may detect the milk 910 from each of the inside-fridge image 903 at the t+1 time point and the inside-fridge image 905 at the t+2 time point.

In addition, the refrigerator 10 may combine a shape of part of an object 920 placed behind the milk 910 in the inside-fridge image 903 at the t+1 time point with a shape of part of the object 920 placed behind the milk 910 in the inside-fridge image 905 at the t+2 time point, and acquire a complete shape of the object 920.

The refrigerator 10 may recognize that the object 920 belongs to a food category of "apple" using the acquired shape of the object 920.

Accordingly, the refrigerator 10 can recognize a category of food using continuous images acquired through a camera.

Figure 10:
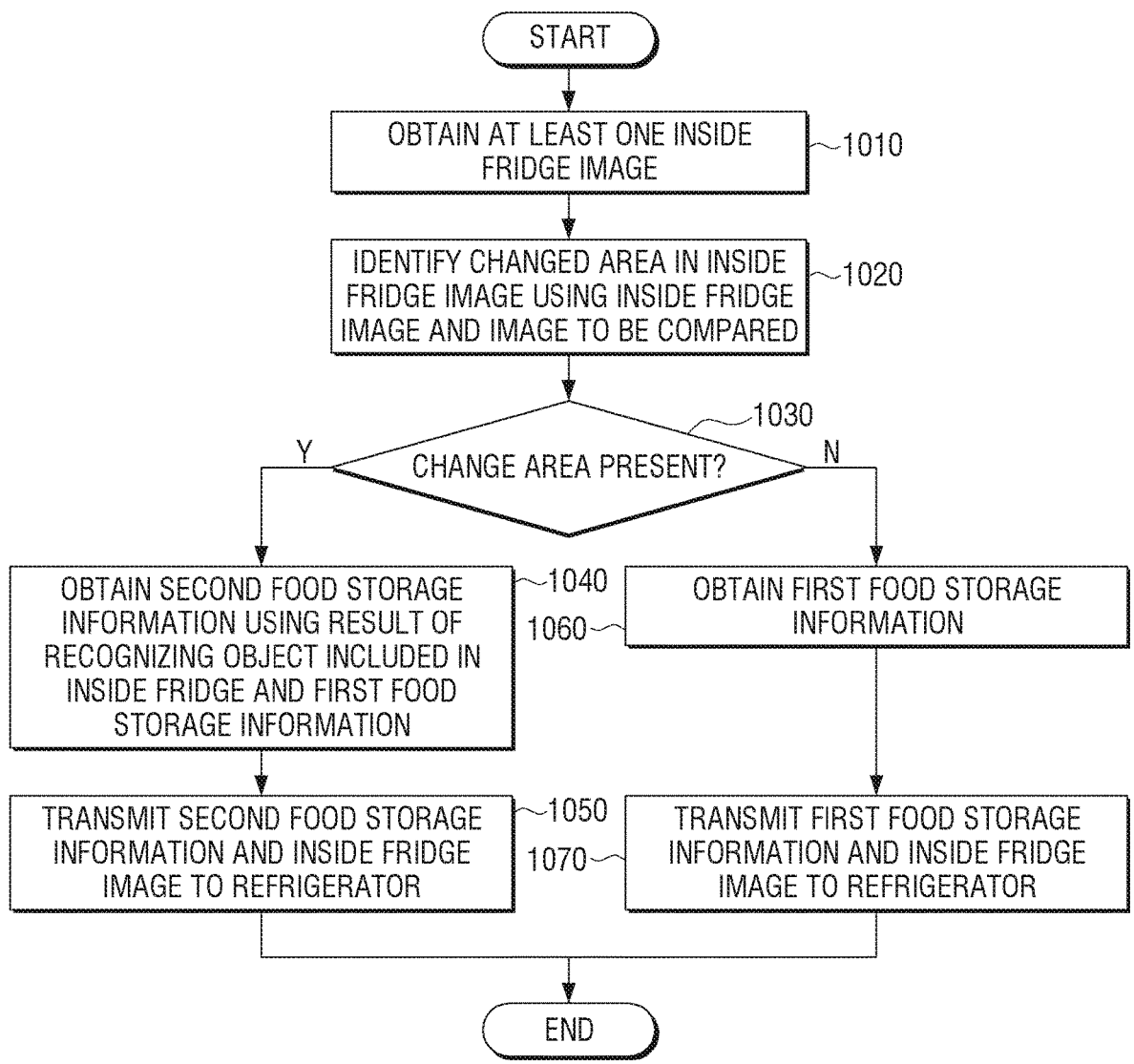
FIG. 10 is a flowchart for a process of executing a food recognition method, according to an embodiment.

FIG. 10 is a flowchart for a process of executing a food recognition method, according to an embodiment.

Referring to the operation 1010, the server 20 may acquire at least one inside-fridge image. For example, the server 20 may receive an inside-fridge image generated by capturing a storage room of the refrigerator 10 using a camera included in the refrigerator 10. For example, when an event that a door is opened and then closed occurs, the refrigerator 10 may capture an inside-fridge image.

Referring to at operation 1020, the server 20 may identify a changed area in the inside-fridge image using the inside-fridge image and an image to be compared.

For example, the server 20 may change the image to be compared and the inside-fridge image to an image emphasizing an edge component, and then compare the acquired shapes of the objects on the basis of the edge component and identify the change area.

According to an embodiment, the server 20 may acquire the change area by using a pixel difference value. For example, the server 20 may calculate the respective differences between a red pixel value (R), green pixel value (G) and blue pixel value (B) included in the image to be compared and R, G and B values of the inside-fridge image, and identify the change area.

According to an embodiment, the server 20 may acquire the change area by using an artificial intelligence algorithm. For example, the server 20 may identify a change area in which a change is made in at least one inside-fridge image by applying the at least one inside-fridge image and an image to be compared to a food change sensing model which is trained with an image, an image which is identical to the image but includes at least some parts with change, and information about locations with change as data for learning.

At operation 1030, the server 20 may identify whether a change area is present or not.

At operation 1040, if the change area is present, the server 20 may acquire second food storage information using a result of recognizing an object included in an inside-fridge image and first food storage information.

According to an embodiment, the server 20 may change the image to be compared and the inside-fridge image to an image emphasizing an edge component, then find a shape of an acquired object based on the edge component, and compare the shape of the object with a data stored in the server 20 and recognize a food category to which the object belongs.

According to an embodiment, when the object is recognized as a processed food, the server 20 may recognize a category to which the processed food belongs and/or a brand name of the processed food by using an additional data additionally stored in the server 20.

According to an embodiment, the server 20 may sense the object by using an artificial intelligence algorithm, and recognize a food category to which the sensed object belongs. For example, the server 20 may sense the object by applying the inside-fridge image to a food recognition model which is trained with an image in which food is present, a category to which the food belongs, and information about a place where the food is located in the image as a data for learning, and may recognize a food category to which the object belongs.

According to an embodiment, as a result of recognizing the object by using a food identification model, when the object is recognized as a processed food, the server 20 may recognize a category of processed food to which the object belongs and/or a brand name of the processed food by using a processed food recognition model. For example, the server 20 may recognize a category of processed foods detected in the inside-fridge image and/or a brand name of processed foods in the processed food database by using a processed food search model which is trained based on image similarity with multiple images for the same processed food, a category of processed food, and a brand name of processed food as a data for learning.

According to an embodiment, in a case that a food that is not recognizable as being hidden by other food is detected, the server 20 may acquire new food storage information by using food information acquired from the first food storage information together with the inside-fridge image.

At operation 1050, the server 20 may transmit the food storage information and the inside-fridge image to the refrigerator.

At operation 1060, in a case that a change area is not present, the server 20 may acquire the first food storage information.

The first food storage information may be, for example, information generated using a result of sensing an object in the image to be compared. In addition, the first food storage information may include, for example, any one or any combination of location information of food sensed in the image to be compared, information about a category to which a food belongs or information about a category of processed food to which a processed food belongs, and a brand name of a processed food.

At operation 1070, the server 20 may transmit the first food storage information and the inside-fridge image to the refrigerator.

Figure 11:
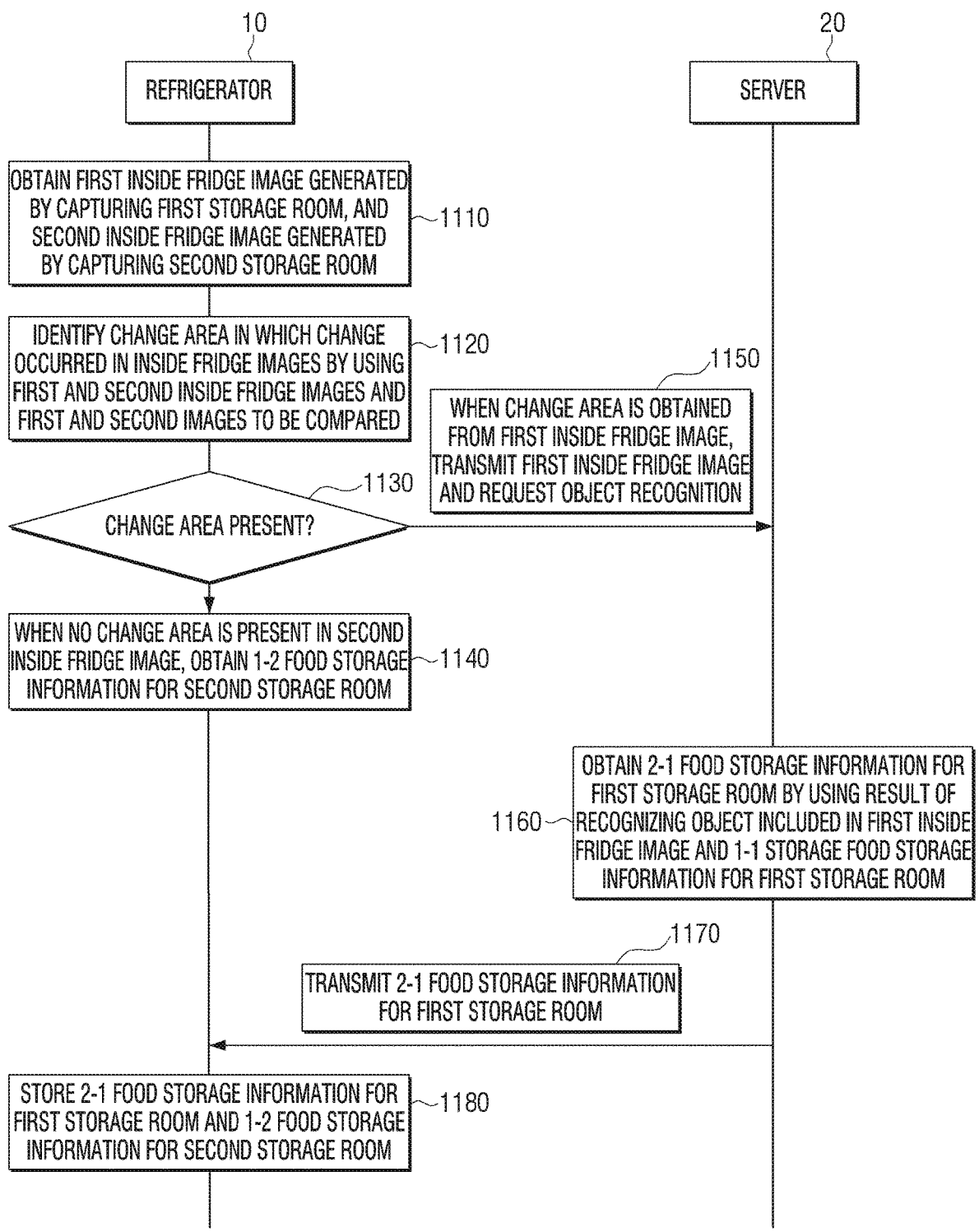
FIG. 11 is a flowchart for a process of executing a food recognition method, according to embodiments.

FIG. 11 is a flowchart for a process of executing a food recognition method, according to embodiments.

At operation 1110, the refrigerator 10 may acquire a first inside-fridge image generated by capturing a first storage room, and a second inside-fridge image generated by capturing a second storage room.

At operation 1120, the refrigerator 10 may use the first inside-fridge image, the second inside-fridge image, the first image to be compared, and the second image to be compared, and identify a change area in which a change is made in the inside-fridge images.

The first image to be compared and the second image to be compared may, for example, images generated by capturing the first storage room and the second storage room, which may be images transferred to the server 20 in which a food is sensed and recognized, and transferred to the refrigerator 10.

At operation 1130, the refrigerator 10 may identify whether a change area is present or not.

At operation 1140, when a change area is not present in the second inside-fridge image, the refrigerator 10 may acquire 1-2 food storage information for the second storage room.

At operation 1150, when a change area is acquired from the first inside-fridge image, the refrigerator 10 may request object recognition while transmitting the first inside-fridge to the server 20.

At operation 1160, the server 20 may acquire 2-1 food storage information for the first storage room by using a result of recognizing an object included in the first inside-fridge image and the 1-1 food storage information for the first storage room.

At operation 1170, the server 20 may transmit the 2-1 food storage information for the first storage room to the refrigerator 10.

At operation 1180, the refrigerator 10 may store the 2-1 food storage information for the first storage room and the 1-2 food storage information for the second storage room.

Figure 12:
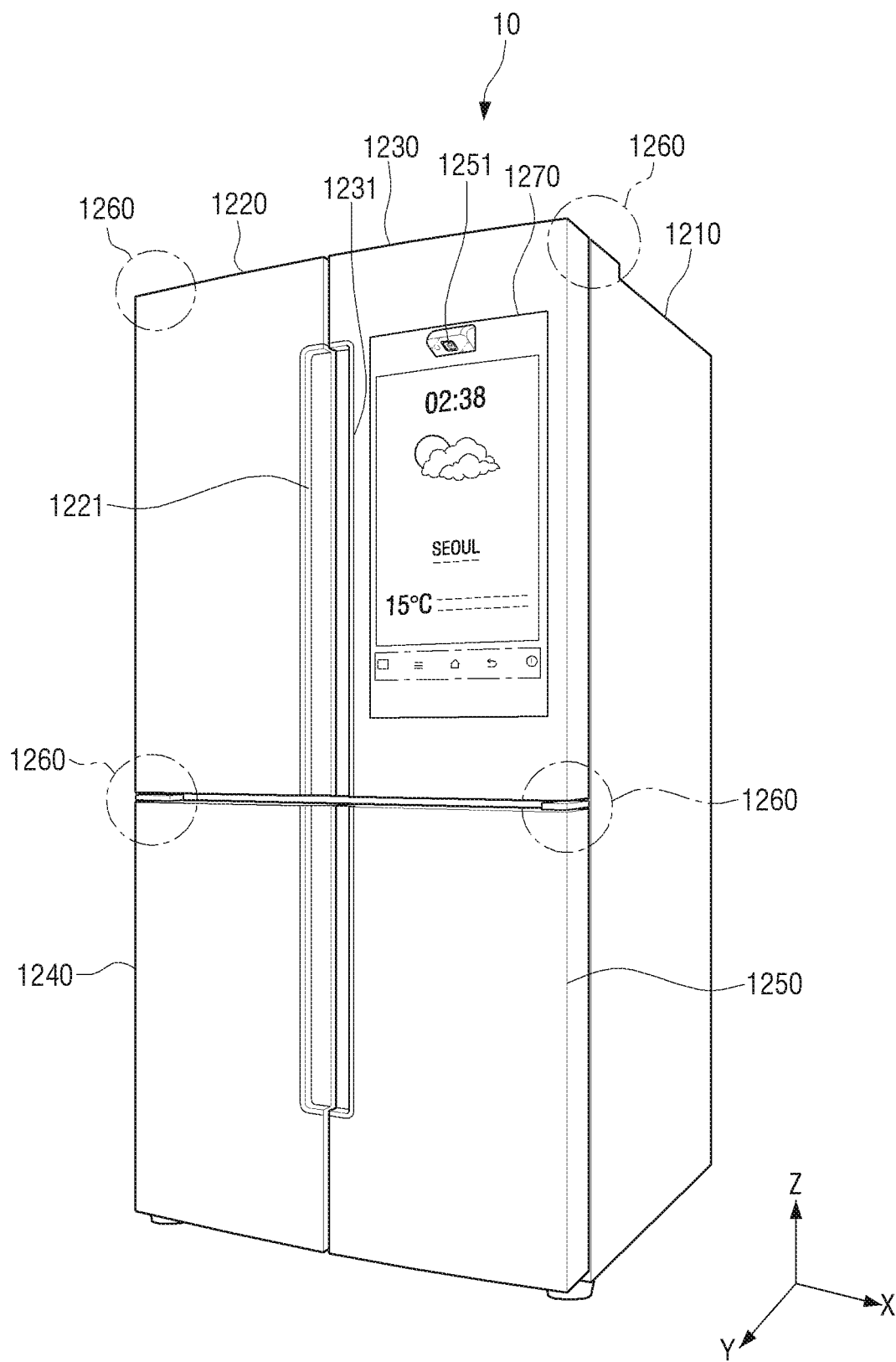
FIG. 12 is a perspective view briefly illustrating a refrigerator with a camera and a display, according to an embodiment.
Figure 13:
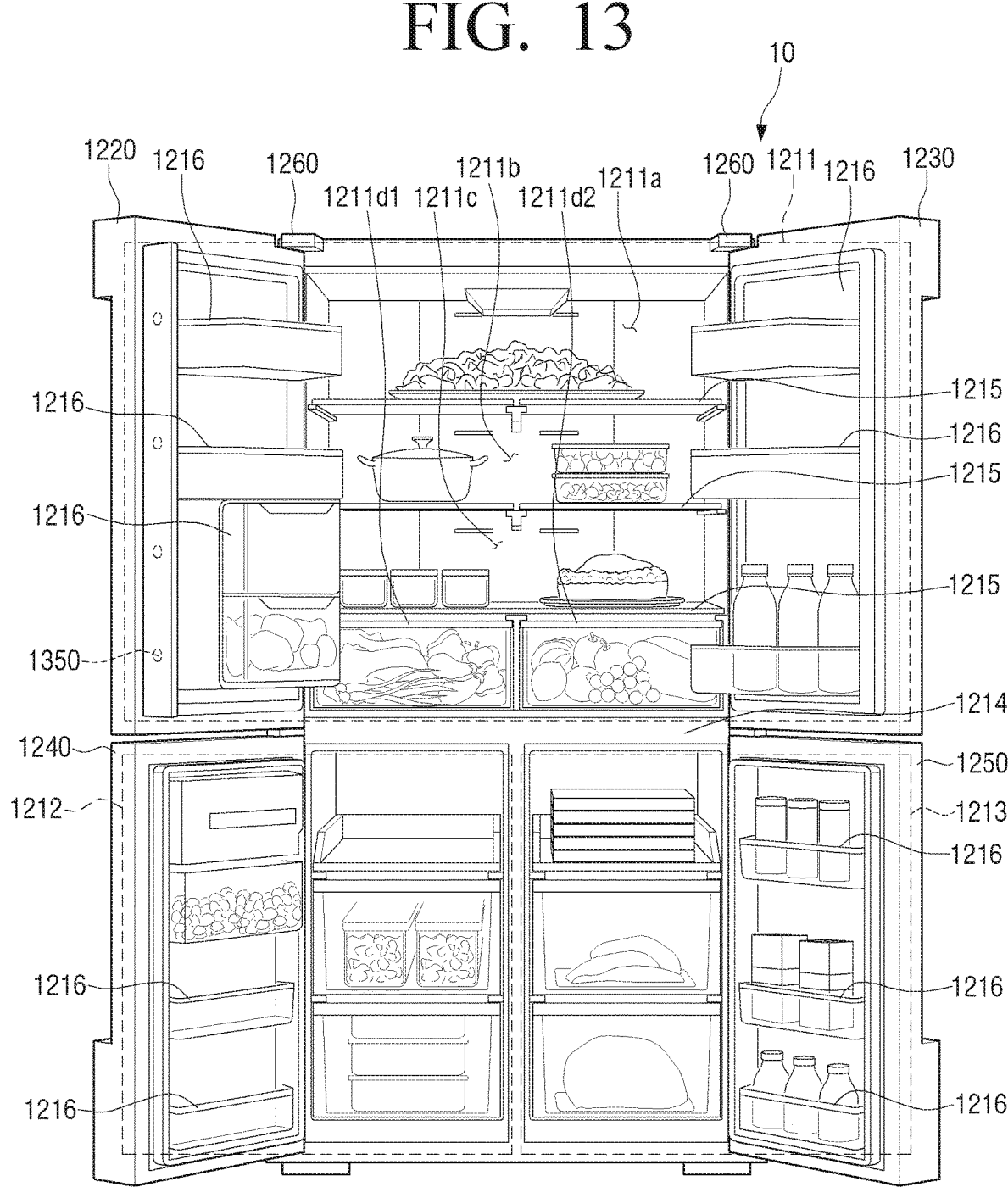
FIG. 13 is a front view briefly illustrating a refrigerator with all doors opened, according to an embodiment.

FIG. 12 is a perspective view briefly illustrating a refrigerator with a camera and a display, according to an embodiment. FIG. 13 is a front view briefly illustrating a refrigerator with all doors opened, according to an embodiment.

Referring to FIGS. 12 and 13, a refrigerator 10 includes a main body 1210, a storage 1211, 1212, 1213, a door 1220, 1230, 1240, 1250, and a hinge 1260 which connects each of the doors 1220, 1230, 1240, 1250 with the main body 1210. A display (or a touch screen, 1270) which displays a content may be positioned on at least one (e.g., either one or both of a right door 1230 and a left door 1220) of a plurality of doors.

A camera may be positioned on at least one (e.g., either one or both of the right door 1230 and the left door 1220) of the plurality of doors. A proximity sensor part may be positioned to be adjacent (e.g., within a radius of 500 mm) to the camera. In addition, a microphone may be positioned on at least one (e.g., either one or both of the right door 1230 and the left door 1220) of the plurality of doors.

The refrigerator 10 may be divided into types according to a shape of a storage and a door. A top mounted freezer (TMP) type refrigerator includes a freezer which is formed on an upper surface of the storage horizontally partitioned by a partition and a cold room which is formed on the lower side of the storage. A bottom mounted freezer (BMF) type refrigerator includes a refrigerator which is formed on an upper side of a storage horizontally partitioned by a partition and a freezer which is formed on the lower side of the storage.

A side by side (SBS) type refrigerator includes a freezer which is formed on one side of the storage vertically partitioned by a partition and a cold room which is formed on the other side of the storage. A French door refrigerator (FDR) refrigerator includes a cold room which is formed on an upper side of the storage horizontally partitioned by a partition and a freezer which is formed on a lower side of the storage. A cold room on the upper side may be opened and closed by a pair of doors. In the FDR refrigerator, both the upper cold room and the lower cold room may be opened and closed by a pair of doors.

The main body 1210 includes an inner case which forms the storage room 1211 to 1213, an outer case which forms an exterior of the refrigerator, and an insulator which maintains a temperature difference between the inner case and the outer case. An insulation material may prevent a cold inner air from leaking outside, and prevent the outside warm air from entering the storage room 1211 to 1213.

The main body 1210 includes a cool air supply part which supplies cool air to the storage room 1211 to 1213. The cool air supply part may include a compressor for compressing a refrigerant, a condenser, an expansion valve, an evaporator, and a pipe.

The storage room 1211 to 1213 is divided by a partition 1214. The storage 1211 to 1213 is divided into a lower freezer storage room 1212 and 1213 (hereinafter referred to as "freezer") and a cold storage room 1211 (hereinafter referred to as "cold room" above the freezer room 1212 and 1213. The storage 1212 may be set to a temperature of over zero (e.g., between 0° C. to 7° C.) or below zero (e.g., between −1° C. to 5° C.) and store water, beverages, food ingredient, and cold or frozen food. Water or beverages may be stored in a beverage container.

The cold room 1211 from among the storage 1211 to 1213 which is divided by a partition 1214 may include one or more shelves 1215 and one or more storage boxes 1216.

The cold room 1211 is attached to one side (e.g., left side) of the storage 1211 and a second door 1230 which is adjacent to the first door 1220 and positioned on the other side (e.g., right side) of the storage room 1211. The first door 1220 and/or the second door 1230 may be rotated at an angle (e.g., 300° or less) set by each hinge 1260 and open or close (e.g., attach or detach) a front surface of the storage 1211. The first door 1220 may be rotated the opposite way to a rotation direction of the second door 1230 and open or close the storage room 1211. The positions of the first door 1220 and the second door 1230 may be mutually changed.

The first door 1220 is rotated at an angle (e.g., 300° or less) set by the hinge 1260 and open or close a portion of the front surface of the storage room 1211 (e.g., between 35% to 70% of the front surface of the storage room 1211).

A dispenser which provides water, ice or sparkling water to the front surface (e.g., +y-axis direction) of the first door 1220 and/or a grabbable handle.

The second door 1230 is rotated at an angle (e.g., 300° or less) set by a hinge 1260 and open or close a portion of the front surface of the storage room 1211 (e.g., between 35% to 70% of the front surface of the storage room 1311). The second door 1230 may include a grabbable handle 1231. A handle 1221 of the first door 1220 and the handle 1231 of the second door 1230 are positioned to be spaced apart in the left and right directions based on a center area of the storage room 1211.

A function and stored setting of the refrigerator 10 may be displayed on the front surface (e.g., +y-axis direction) of the second door 1230. A user input (e.g., touch or selection of a button may be received in the front surface of the second door 1230. A display (or the touch screen 1270) which is capable of displaying (or executing) a screen of an application (including a widget) may be positioned at the front surface of the second door 1230. The button may be included in the display or may be configured separately from the display. The button may be a button which is displayed on a touch screen, a touch button or a physical button.

A vegetable compartment 1211d1 and 1211d2 is positioned below the storage room 1211. The vegetable compartment 1211d1, 1211d2 may be withdrawn (e.g., slid or rolled) toward the front side (e.g., y-axis direction).

The storage room 1212 may have a door 1240 on one side. The storage room 1213 may have a door 1250 on one side. The storage room 1212 and 1213 may be combined into one storage room (e.g., like the storage room 1311). One storage room may have a door on each of the left side and the right side just like the storage room 1211. According to the embodiments, the storage room 1211, 1212 and 1213 may be divided by a shelf, etc. into, for example, a first storage room 1211*a,* a second storage room 1211*b,* a third storage room 1211*c,* etc. In addition, the refrigerator may have a drawer.

The refrigerator 10 may further include a front camera 1251 on an outer side of the second door 1230. The refrigerator 10 may recognize a person positioned on a front surface of the refrigerator 10 using the front camera 1251. In addition, the refrigerator 10 may further include the display 1270. The display 1270 may include the display 11 of FIG. 1A and the display 510 of FIG. 5.

Figure 14:
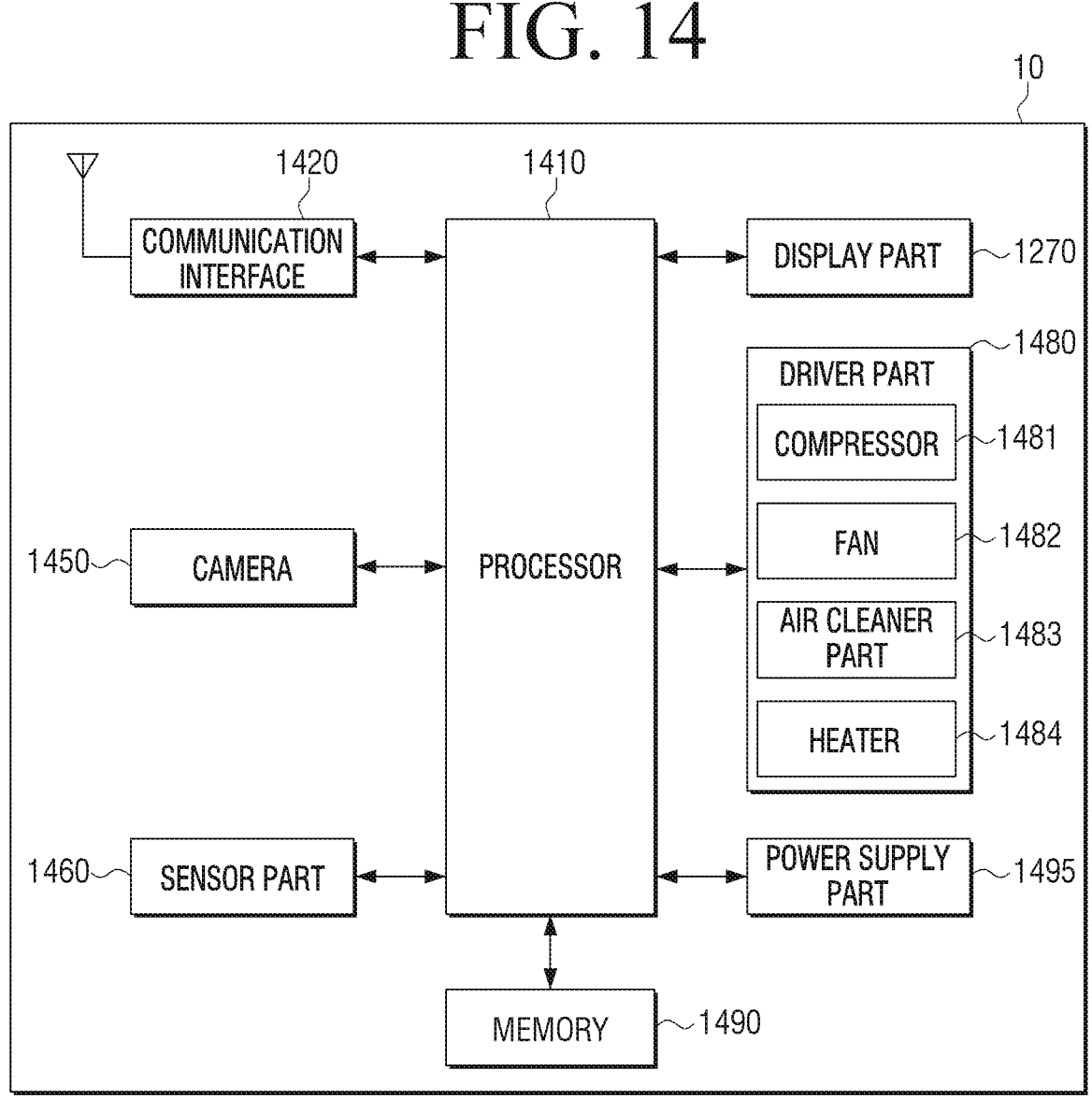
FIG. 14 is a block diagram briefly illustrating a refrigerator, according to an embodiment.

FIG. 14 is a block diagram briefly illustrating a refrigerator, according to an embodiment.

Referring to FIG. 14, a refrigerator 10 may be functionally connected with an external apparatus by using a communication interface 1420. The communication interface 1420 may include the communication interface 220 of FIG. 2. The external apparatus may include either one or both of a user terminal and a server 20.

The refrigerator 10 may transmit operation information corresponding to an operation (e.g., temperature control of each storage) of the refrigerator and state information corresponding to a state (e.g., normal, abnormal, and the like) of the refrigerator 10 to the external apparatus via the communication interface 1420, or may receive control information (e.g., a control command corresponding to quick freezing of the refrigerator 10) from an external apparatus.

The refrigerator 10 may include a processor 1410, a communication interface 1420, a camera 1450, a sensor part 1460, a display 1270 (or display part), a driver part 1480, a memory 1490, and a power supply part 1495.

The processor 1410 (or controller) may include one or more processors. The processor 1410 may include the processor 210 of FIG. 2. In addition, the processor 1410 may store a non-volatile memory which includes ROM that stores a control program for controlling the refrigerator 10 and a volatile memory which includes RAM that stores a signal or data inputted from outside the cook top 10 or is used as a storage area with respect to various operations performed on the refrigerator 10. The RAM may be used as a storage area with respect to control information received from an external source, operation information of the refrigerator 10 or state information of the refrigerator 10.

The processor 1410 serves to control a signal flow between the overall operation of the refrigerator 10 and the internal components of the refrigerator 10 and process data. The processor 1410 may control a power supplied to internal elements by using the power supply part 1495.

The processor 1410 may control a communication interface 1420, a camera 1450, a sensor part 1460, a display 1270, a driver part 1480, a memory 1490, and a power supply part 1495.

The communication interface 1420 may connect with an external apparatus via a mobile communication network, a wireless LAN communication network, or a near field communication network by using one antenna or two or more antennas under the control of the processor 1410. The wireless LAN communication may be wirelessly connected with an access point (AP) at a location where the AP is installed under the control of the processor 1410. For example, the wireless LAN communication may include a Wi-Fi communication. The near field communication may include a Bluetooth communication, a Bluetooth low energy communication, an infrared data association (IrDA) communication, a ultra-wideband (UWB) communication, a magnetic security transmission (MST) communication and/or an NFC communication. According to the embodiments, the term "communication interface" may be connect with an external device via a mobile communication, a wireless LAN communication and/or near field communication.

The camera 1450 may capture a still image or record a video under the control of the processor 1410. The camera 1450 may include the camera 230 of FIG. 2 or the camera 1251 of FIG. 12. The camera 1450 may capture a still image or record a video for registration and/or management of food. The camera 1450 may capture an iris of the user under the control of the processor 1410. The camera 1450 may include a front camera 1251 located on a front surface of the refrigerator 10, and an indoor camera located inside the refrigerator 10. In addition, an iris capturing camera for capturing an iris of a user may be positioned on one side of the front camera 1251.

The front camera 1251 may be inclined at a set angle (e.g., less than 85°) towards a front side (e.g., +y-axis direction) based on the front side (or surface) of the door of the refrigerator 10. The above-mentioned setting angle may be 75 degrees or less or may be 35 degrees or more. In addition, the above-mentioned setting angle may be 65 degrees or less or may be 15 degrees or more.

One of the front camera 1251 and the indoor camera may include an auxiliary (e.g., flash) which provides an amount of light for capturing. In addition, an auxiliary light source (e.g., an LED for iris recognition) for capturing an iris may be positioned on a front surface of the refrigerator 10.

One front camera 1251 or a plurality of front cameras 1251 may be included. One or more indoor cameras may be positioned on a rear surface of the door 1220 to 1250 which faces the storage room 1211 to 1213 according to an area of the storage room. For example, one or more indoor cameras may be positioned on a rear surface of the door 1220 and 1230 which faces the storage room 1211. One or more indoor cameras may be positioned on a rear surface of the door 1240 which faces the storage 1212. In addition, one or more indoor cameras may be positioned on a rear surface of the door 1250 which faces the storage room 1213.

The processor 1410 may control an image captured through one of the front camera 1251 and the indoor camera to be stored in the memory 1490.

The sensor part 1460 may detect a peripheral state (e.g., illumination) of the refrigerator 10 and/or an internal state (e.g., temperature of storage room) of the refrigerator 10 through one or a plurality of sensors.

The sensor part 1460 may include any one or any combination of a proximity sensor part for detecting whether a user approaches to the refrigerator 10, and one or a plurality of temperature sensor parts for detecting a temperature of a storage (e.g., a freezer, a cold room, a vegetable room, and the like) of the refrigerator 10. In addition, an illumination sensor part for sensing an intensity of light surrounding the refrigerator 10 corresponding to a change of light of the display 1270 may be included. One of the proximity sensor part and the illumination sensor part from among the sensor part 1460 may be located on a front surface of the door of the refrigerator 10. In addition, the temperature sensor part may be disposed inside the refrigerator to correspond to the storage room.

It would be easily understood by those skilled in the art that a sensor type included in the sensor part 1460 may be added, modified or deleted according to a performance of the refrigerator 10.

The display 1270 may provide (or display) a graphical user interface (GUI) corresponding to various services (e.g., voice call, video call, data transmission, broadcasting reception, photo capturing, video content viewing, electronic payment including mobile payment, etc.). In an embodiment, the display 1270 may configured to include a touch screen.

In the touch screen, the display panel and the touch panel 172 may be implemented as being integral (e.g., in-cell type touch screen or on-cell type touch screen).

The touch screen may include an edge touch panel for receiving a user input, and an edge display panel for displaying a content. The edge touch panel and the edge display panel may be implemented as being integral as described above.

The touch screen may transmit, to a touch screen controller, an analog signal corresponding to a single touch or multi-touch input through a home screen or a GUI. The touch screen may receive a single touch or multi-touch through a body (e.g., fingers including a thumb) of the user or an input pen (e.g., stylus).

The driver part 1480 may include any one or any combination of a compressor, a fan, a filter and a heater operating under the control of the processor 1410. The driver part 1480 may further include a lighting (or deodorizing device).

A compressor 1481 may compress a refrigerant which is a working fluid of a refrigeration cycle, under the control of the processor 1410. The refrigeration cycle may include a condenser converting a refrigerant in a compressed air state into a refrigerant in a liquid state, an expander decompressing the refrigerant in the liquid state, and an evaporator evaporating the decompressed refrigerant in the liquid state. The processor 1410 may control a temperature of a storage room through evaporation of the refrigerant in the liquid state. In addition, the refrigerator 10 may control the temperature of the storage room through a peltier module using a peltier effect, and a magnetic cooling apparatus using a magnetocaloric effect.

A fan 1482 may circulate an outside air under the control of the processor 1410. The air heated by a cooling cycle may be cooled down by performing heat exchange through an outside air.

An air cleaning part 1483 may sterilize (or eliminate) bacteria floating inside, or attached to, the storage room under the control of the processor 1410. The air cleaning part 1483 may include an ion sterilization cleaning part.

A heater 1484 may perform defrosting under the control of the processor 1410. The heater 1484 may include a defrost heater.

The memory (or storage) 1490 may, under the control of the processor 1410, store a signal or data (e.g., corresponding to food management (or food recognition)) input or output to correspond to an operation of an element. The memory 1490 may include the memory 240 of FIG. 2. The memory 1490 according to an embodiment may store food storage information relating to food stored in the refrigerator 10.

The term "module" as used herein includes units made up of hardware, software, or firmware, and may be used interchangeably with terms such as logic, logic blocks, components, or circuits. A "module" may be an integrally constructed component or a minimum unit or part thereof that performs one or more functions. For example, according to an embodiment, the module may be implemented in the form of an application-specific integrated circuit (ASIC).

The embodiments of the disclosure may be implemented as a software including one or more instructions stored in a storage medium (e.g., memory) that is readable by a machine (e.g., refrigerator 10 or server 20). For example, a processor (e.g., processor 210) of the machine (e.g., refrigerator 10) may call at least one instruction from among the one or more instructions stored in the storage medium, and execute the called instruction. This enables the machine to be managed to perform at least one function according to the called at least one instruction. The one or more instructions may include a code generated by a compiler or a code executable by an interpreter. A machine-readable storage medium may be provided in the form of a non-transitory storage medium. Herein, the term "non-transitory" only denotes that a storage medium does not include a signal (e.g., electromagnetic field) but is tangible, and does not distinguish the case in which a data is semi-permanently stored in a storage medium from the case in which a data is temporarily stored in a storage medium.

According to an embodiment, the method according to the above-described embodiments may be provided as being included in a computer program product. The computer program product may be traded as a product between a seller and a consumer. The computer program product may be distributed online in the form of machine-readable storage media (e.g., compact disc read only memory (CD-ROM)) or through an application store (e.g., Play Store™ and App Store™) or distributed online (e.g., downloaded or uploaded) directly between to users (e.g., smartphones). In the case of online distribution, at least a portion of the computer program product may be at least temporarily stored or temporarily generated in a server of the manufacturer, a server of the application store, or a machine-readable storage medium such as memory of a relay server.

According to the embodiments, the respective elements (e.g., module or program) of the elements mentioned above may include a single entity or a plurality of entities. According to the embodiments, at least one element or operation from among the corresponding elements mentioned above may be omitted, or at least one other element or operation may be added. Alternatively or additionally, a plurality of components (e.g., module or program) may be combined to form a single entity. In this case, the integrated entity may perform functions of at least one function of an element of each of the plurality of elements in the same manner as or in a similar manner to that performed by the corresponding element from among the plurality of elements before integration. The module, a program module, or operations executed by other elements according to variety of embodiments may be executed consecutively, in parallel, repeatedly, or heuristically, or at least some operations may be executed according to a different order, may be omitted, or the other operation may be added thereto.

What is claimed is:

1. A server comprising:
a memory storing instructions; and
at least one processor configured to execute the instructions to:
obtain at least one inside-fridge image captured in a refrigerator;
identify whether a change area in which a change is occurred in the inside-fridge image, is present by inputting a pre-stored image and the inside-fridge image to a food change sensing model that is stored in the memory;
based on the change area being not in the inside-fridge image, obtain first food storage information, using a first result of recognizing the pre-stored image;
based on the change area being in the inside-fridge image, obtain second food storage information, using the first food storage information and a second result of recognizing an object included in the inside-fridge image; and transmit, to the refrigerator, the inside-fridge image and either one or both of the first food storage information and the second food storage information,
wherein the at least one inside-fridge image comprises an image capturing inside of the refrigerator based on an event that a door of the refrigerator is opened and then closed,
wherein the food change sensing model uses at least one neural network which is trained with a first training image of a training area, a second training image of the training area in which a part of the training area is changed, and location information about a position of the part at which the training area is changed, as a training data, to identify the change area;
wherein the at least one processor is further configured to, based on the object being recognized as a processed food, recognize a category of processed food included in the inside-fridge image using a processed food recognition model; and
wherein the processed food recognition model is trained with multiple images for a same processed food, a processed food category of the same processed food, and a brand name of the same processed food.

2. The server as claimed in claim 1, wherein the at least one processor is further configured to identify whether the change area is in the inside-fridge image, based on a difference value between a first value of each of first pixels included in the pre-stored image and a second value of each of second pixels included in the inside-fridge image.

3. The server as claimed in claim 1, wherein the at least one processor is further configured to:
apply, to the inside-fridge image, either one or both of a first image correction processing to correct blurring of the inside-fridge image and a second image correction processing to increase a clarity of the inside-fridge image; and
identify whether the change area is in the inside-fridge image to which the either one or both of the first image correction processing and the second image correction processing are applied.

4. The server as claimed in claim 1, wherein the at least one processor is further configured to:
change the inside-fridge image to a new image emphasizing an edge component of the inside-fridge image; and
based on the inside-fridge image being changed to the new image, recognize the object included in the new image, based on a shape of the object which is identified based on the emphasized edge component.

5. The server as claimed in claim 1, wherein the at least one processor is further configured to, based on the change area being in the inside-fridge image, recognize the object included in the inside-fridge image, in the change area.

6. The server as claimed in claim 1, wherein the inside-fridge image comprises a first inside-fridge image and a second inside-fridge image, and
wherein the at least one processor is further configured to obtain a third result of recognizing another object included in the second inside-fridge image but not being recognized in the first inside-fridge image.

7. A refrigerator comprising:
a camera configured to capture a storage room storing food;
a communication interface;
a processor;
a display; and
a memory storing one or more instructions that cause the processor to:
control the camera to capture an inside-fridge image, based on an event that a door of the refrigerator is opened and then closed; and
control the communication interface to:
transmit the inside-fridge image, to a server;
receive, from the server, the inside-fridge image and either one or both of first food storage information and second food storage information corresponding to the inside-fridge image, wherein the server is configured to identify whether a change area in which a change is occurred in the inside-fridge image, is present by inputting a pre-stored image and the inside-fridge image to a food change sensing model, and based on the whether the change area being occurred, transmit either one or both of the first food storage information and the second food storage information to the refrigerator, and
wherein the food change sensing model uses at least one neural network which is trained with a first training image of a training area, a second training image of the training area in which a part of the training area is changed, and location information about a position of the part at which the training area is changed, as a training data, to identify the change area;
control the display to display the inside-fridge image;
based on a first user input to select a food included in the inside-fridge image displayed on the display, control the display to display at least one candidate category to which the selected food belongs; and
based on a second user input to select one of the at least one candidate category, identify the selected one of the at least one candidate category, as a category of the food.

8. The refrigerator as claimed in claim 7,
wherein the one or more instructions further cause the processor to:
control the display to display a recipe providing execution object;
based on a user input to select the recipe providing execution object displayed on the display, control the communication interface to:
transmit the category of the food included in the inside-fridge image, to the server; and
receive a recipe that is obtained by the server using the category; and
control the display to display the received recipe.

9. The refrigerator as claimed in claim 7,
wherein the one or more instructions further cause the processor to:
control the display to display a food purchase website link execution object;
based on a user input to select the food purchase website link execution object displayed on the display, control the communication interface to access a food purchase website selling a food category corresponding to a food that is previously included in the inside-fridge image but not currently included in the inside-fridge image; and
control the display to display the food purchase website.

10. The refrigerator as claimed in claim 7,
wherein the one or more instructions further cause the processor to:

control the display to display a health information displaying execution object; and based on a user input to select the health information displaying execution object displayed on the display, control the display to display health information of a user, using a calorie of a food that is previously included in the inside-fridge image but not currently included in the inside-fridge image.

11. The refrigerator as claimed in claim 7, comprising:

a first camera;

a second camera;

a first storage room; and a second storage room, and wherein the one or more instructions cause the processor to:

control the first camera to capture a first inside-fridge image of the first storage room;

control the second camera to capture a second inside-fridge image of the second storage room;

identify whether an area changes in each of the first inside-fridge image and the second inside-fridge image, by comparing a pre-stored image to a respective one of the first inside-fridge image and the second inside-fridge image;

based on the area being not changed in the first inside-fridge image, obtain the first food storage information, using a first result of recognizing the pre-stored image; and based on the area being changed in the second inside-fridge image, control the communication interface to:

transmit the second inside-fridge image, to the server; and receive, from the server, the second food storage information obtained by the server using the first food storage information and a second result of recognizing an object included in the second inside-fridge image.

12. The refrigerator of claim 11, wherein the one or more instructions further cause the processor to:

based on the area being not changed in the second inside-fridge image, obtain the first food storage information; and based on the area being changed in the first inside-fridge image, control the communication interface to:

transmit the first inside-fridge image, to the server; and receive, from the server, third food storage information obtained by the server using the first food storage information and a third result of recognizing another object included in the first inside-fridge image.

* * * * *